US005858967A

United States Patent [19]
Weigle et al.

[11] Patent Number: 5,858,967
[45] Date of Patent: Jan. 12, 1999

[54] APPETITE SUPRESSION FACTOR AND RELATED METHODS

[75] Inventors: David S. Weigle, Bainbridge Island; Joseph L. Kuijper, Bothell; John W. Forstrom, Seattle, all of Wash.

[73] Assignees: University of Washington; Zymogenetics, Inc., both of Seattle, Wash.

[21] Appl. No.: 938,001

[22] Filed: Sep. 19, 1997

Related U.S. Application Data

[63] Continuation of Ser. No. 486,459, Jun. 7, 1995, abandoned, which is a continuation-in-part of Ser. No. 419,214, Jul. 10, 1995, abandoned, which is a continuation-in-part of Ser. No. 377,068, Jan. 20, 1995.

[51] Int. Cl.$^6$ .......................... A01N 37/18; A61K 37/00; C12P 21/06
[52] U.S. Cl. ............................... 514/2; 435/69.1
[58] Field of Search .................... 424/78.1, 574; 435/69.1, 70.1, 71.1, 514; 2/536; 536/23.5

[56] References Cited

U.S. PATENT DOCUMENTS

| 4,197,319 | 4/1980  | Betz et al. .   |         |
|-----------|---------|----------------|---------|
| 4,489,059 | 12/1984 | Rossini et al. .|         |
| 4,491,578 | 1/1985  | Peiken .       |         |
| 4,588,685 | 5/1986  | Knoll et al. ............................. | 435/68.1 |
| 4,613,586 | 9/1986  | Barchas et al. .|         |
| 5,013,722 | 5/1991  | Danho et al. . |         |
| 5,169,852 | 12/1992 | Barchas et al. .|         |
| 5,378,816 | 1/1995  | Pungor et al. .|         |
| 5,552,524 | 9/1996  | Basinski et al. .|        |

FOREIGN PATENT DOCUMENTS

| 0060776    | 9/1982  | European Pat. Off. . |
| 0566410    | 10/1993 | European Pat. Off. . |
| 2292382    | 2/1996  | United Kingdom .     |
| WO 96/05309| 2/1996  | WIPO .               |

OTHER PUBLICATIONS

Murakami et al., *Biochemical and Biophysical Research Communications* 209(3):944–952, 1995.
Hulsey et al., *Physiology & Behavior* 52: 1141–1149, 1992.
Ako et al., *Life Sciences* 42: 877–888, 1988.
Nagy, *Pharmacology Biochemistry and Behavior* 48(1): 17–22, 1994.
Sniderman et al., *Ann. Med.* 26: 389–393, 1994.
Kidwai et al., *Mol. Cell. Biol.* 91: 117–122, 1989.
Bellinger et al., *Pharmacology Biochemistry and Behavior* 47(3): 659–666, 1994.
Zhang et al., *Nature* 372: 425–432, 1994.
Hutson et al., *Clin. Res. 40*: 60A, 1992.
Weigle, *The FASEB Journal* 8: 302–310, 1994.
Bowie et al., "Deciphering the message in protein sequences: tolerance to amino acid substitions" *Science* (1990) 247:1306–1310.
Callard et al., *The Cytokine FactsBook*, Academic Press, London, pp. 31 and 139.
Campfield et al., "Recombinant mouse OB protein: Evidence for a peripheral signal linking adiposity and central neural networks" *Science* (1995) 269: 546–549.
Chen, "A single intracerebroventricular injection of dexamethasone elevates food intake and plasma insulin and depresses metabolic rates in adrenalectomized obese (ob/ob) mice" *J. Nutrition*(1995).
Considine et al., "Evidence against either a premature stop codon or the absence of abese gene mRNA in human obesity" *J. Clin. Invest.* (1995) 95:2986–2988.
Dubuc, "Effects of limited food intake on the obese–hyperglycemic syndrome" *Am. J. Phys.* (1976) 230(6):1474–1479.
Friedman et al., "Tackling a weighty problem" *Cell* (1992) 69:217–220.
Halaas et al., "Weight–reducing effects of the plasma protein encoded by the obese gene" *Science* (1995) 269:543–546.
Harlow et al., *Antibodies, A Laboratory Manual*, Cold Spring Harbor Laboratory, 1988, pp. 53–137.
King, "Lipostatic control of body weight: Evidence of humoral mediation" *Phys. Psych.* (1976) 4(4):405–408.
Knoll, "Satietins, $\alpha_1$–glycoproteins in human plasma with potent, long–lasting and selective anoretic activity" *Med. Res. Rev.* (1987) 7:107–144.
Leighton et al., "The effects of the kappa agonist PD–117302 on feeding behavior in obese and lean Zucker rats" *Pharm. Biochem. Behav.* (1988) 31:425–429.
Maniatis et al., *Molecular Cloning, A Laboratory Manual*, Cold Spring Harbor Laboratory, 1982, pp. 403–433.
Ngo et al., *The Protein Folding Problem and Tertiary Structure Pediction*, Mez et al., eds., Birkhauser, Boston, 1994, pp. 491–495.
Pelleymounter et al., "Effects of the obese gene product on bodyweight regulation in ob/ob mice" *Science* (1995) 269:540–543.
Sambrook et al., *Molecular Cloning, A Laboratory Manual*, Cold Spring Harbor Laboratory Press, 1989, pp. 18.77–18.80.
Williamson et al., "Solution structure of the active domain of tissue inhibitor of metalloproteinases–2. A new member of the OB fold protein family" *Biochem.* (1994) 33:11745–11759.
Zsigmond et al., "Proteolytic degradation of HDL on the fat cell surface is nutritionally regulated" *Biochem. Cell. Bio.* (1989) 67:428–433.

*Primary Examiner*—Karen Cochrane Carlson
*Attorney, Agent, or Firm*—Morrison & Foerster LLP

[57] ABSTRACT

Methods for identifying factors that regulate appetite are disclosed. Preferably, the methods feature determinination of decreased food consumption in selected recipient mammals following administration of a test sample. A product having appetite suppressing activity is also described. In addition, methods for reducing food consumption in a mammal, featuring administration of a pharmaceutical composition comprising a representative appetite suppression factor, are disclosed.

14 Claims, 7 Drawing Sheets

APPETITE SUPRESSION FACTOR AND RELATED METHODS

REFERENCE TO RELATED APPLICATIONS

This application is a continuation and claims the priority benefit of application Ser. No. 08/486,459, filed Jun. 7, 1995, abandoned, which is a continuation-in-part of Ser. No. 08/419,214, filed Apr. 10, 1995, abandoned, which is a continuation-in-part of of Ser. No. 08/377,068, filed Jan. 20, 1995, now pending.

BACKGROUND OF THE INVENTION

Obesity affects an ever-increasing proportion of the population of Western cultures. Nearly one-third of adults in the United States are in excess of their ideal body weight by at least 20%. This results in a major public health problem, because obesity is associated with a multitude of medical problems that include hypertension, elevated blood lipids, coronary artery disease, osteoarthritis and Type II or non-insulin-dependent diabete mellitus (NIDDM). In the United States alone, there are an estimated 6–10 million individuals with NIDDM, including 18% of the population over 65 years of age and most of these individuals are obese (Harris et al. *Diabetes* 36:523–534, 1987). While there appears to be a heterogeneous etiology for NIDDM, obesity alone leads to insulin resistance and NIDDM in individuals that are predisposed to the disease, and it exacerbates the condition in patients already presenting with NIDDM.

Stability of body composition requires that energy intake equals expenditure when integrated over prolonged periods. Since recent human studies have failed to demonstrate active changes in energy expenditure with changes in body composition, it appears likely that energy intake is continually adjusted to preserve a constant total adipose tissue mass. If adipose tissue mass is regulated directly, then there must be some input signaling this quantity to the central nervous system for the purpose of making corrective changes in appetite when total body fat content fluctuates. The nature of this input has been examined in a variety of animal experiments involving induced weight change (Cohn et al., *Yale J. Biol. Med.* 34:598–607, 1962; Harris et al., *Proc. Soc. Exp. Biol. Med.* 191:82–89, 1989; and Wilson et al., *Am. J. Physiol.* 259:R1148–R1155, 1990); lipectomy (Forger et al., *Metabolism* 37:782–86, 1988; Liebel et al., *Ann. N.Y. Acad. Sci.* 131:559–82, 1965; and Chlouverakis et al., *Metabolism* 23:133–37, 1974); plasma transfer from obese or satiated animals to hungry animals (Davis et al., *Science* 156:1247–48, 1967; Davis et al., *J. Comp. Physiol. Psychol.* 67:407–14, 1969; and King, *Physiol. Psychol.* 4:405–08, 1976); and parabiosis between obese and lean animals (Hervey, *J. Physiol.* 145:336–52, 1959; Parameswaran et al., *Am. J. Physiol.* 232:R150–R157, 1977; Nishizawa et al., *Am. J. Physiol.* 239:R344–351, 1980; Harris et al., *Am. J. Physiol.* 257:R326–R336, 1989; Schmidt et al., *Acta Physiol. Acad. Sci. Hung. Tomus* 36:293–98, 1969; Coleman et al., *Diabetologia* 9:294–98, 1973; Harris et al., *Int. J. Obesity* 11:275–83, 1987; and Coleman et al., *Am. J. Physiol.* 217:1298–1304, 1969). From these experiments, there was some evidence that the plasma level of one or more unidentified stable circulating molecules increases in proportion to total body fat content and augments the effect of meal-related satiety signals in the central nervous system.

The search for factors that affect and ultimately control appetite has taken two paths. The first, based on genetic observations, has recently resulted in the cloning of the ob gene (Zhang et al., *Nature* 372:425–32, 1994; by use of positional cloning using mice that were ob/ob mutants. However, while Zhang and others speculated that the ob gene product may be a regulating factor of body fat content, this has not been shown. The second path involves attempts to isolate a discrete factor or factors that regulate body composition based on functional properties.

The isolation of a functional appetite suppression factor (ASF), however, has been unsuccessful, in part due to an inability to reliably determine changes in food consumption as a result of administration of putative appetite suppression factors. The present invention provides a consistent method for identifying and quantitating ASF activity in a test sample, including a sample containing an expressed ob gene product or other factors that regulate appetite.

SUMMARY OF THE INVENTION

It is an object of the present invention to provide methods for identifying a factor that regulates appetite, comprising the steps of establishing a food consumption baseline in a mammal; administering a test sample to the mammal by peripheral injection; and, at least 12 hours after administering the test sample, determining a decrease in food consumption by the mammal, wherein the decrease indicates the presence in the test sample of an appetite suppression factor. In a preferred embodiment, the mammal is an ob/ob mouse.

DETAILED DESCRIPTION OF THE INVENTION

Figure 1:
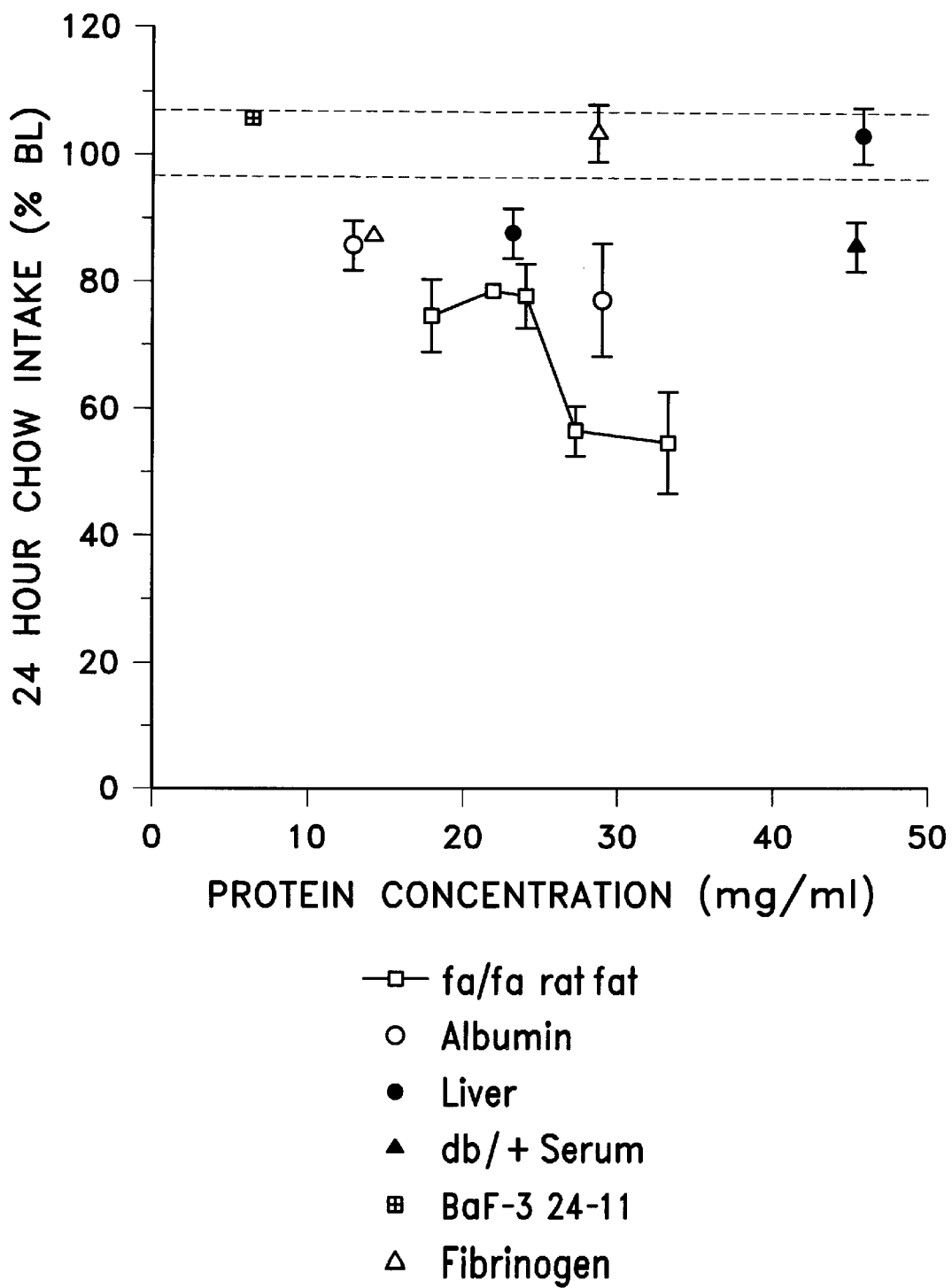
FIG. 1 depicts feeding suppression in normal BALB/c mice that were injected with various concentrations of fa/fa rat adipose conditioned medium. Injection of control preparations at various protein concentrations did not reduce chow intake. fa/fa adipose conditioned medium (□); albumin (○); liver (●); db/+ serum (solid triangle); BAF3 24-11 conditioned medium (square divided into quadrants); fibrinogen (Δ).

Prior to describing the present invention in detail, it may be helpful to define certain terms used herein:

ob/ob mice: Inbred mice that are homozygous for an inactivating mutation at the ob (obese) locus. ob/ob mice are hyperphagic and hypometabolic, and are believed to be deficient in production of circulating satiety factor.

db/db mice: Inbred mice that are homozygous for an inactivating mutation at the db (diabetes) locus. db/db mice display a phenotype similar to that of ob/ob mice, except db/db mice also display a diabetic phenotype. db/db mice are believed to be resistant to the effects of circulating satiety factor.

fa/fa rats: Also known as Zucker rats, fa/fa rats are homozygous for a mutation that is syntenic to the mutation in db/db mice. However, fa/fa rats (and particularly young fa/fa rats) are not as severely diabetic as db/db mice, and thus exhibit a phenotype and characteristics that are similar to ob/ob mice.

Hyperphagia: Ingestion of greater than optimal quantity of food.

Microdissection: For tissue that has been excised and snipped into pea-sized lumps, the process of floating such lumps on the surface of a liquid medium and dissecting such lumps further by snipping with scissors held vertically to the liquid's surface.

Adipose conditioned medium (ACM): Serum-free culture medium that has been incubated with microdissected, excised adipose tissue obtained from a mammalian donor.

Appetite suppression factor (ASF): A factor that, upon administration of an effective dose to an appropriate recipient mammal, down-regulates food intake in that recipient. As used herein, ASF includes the terms "satiety factor", "adipose satiety factor" and "appetite (down-)regulating factor".

ob: As used herein, ob or _ob_ denotes nucleic acid. This designation is distinct from the rodent mutant phenotype designations defined above (i.e., ob/ob mice), which are used in the format "*/*", but not in the singular "*".

_ob_: As used herein, ob denotes protein.

One aspect of the present invention describes methods useful for identifying appetite regulating factors. In a preferred embodiment, the methods are useful for identifying factors that down-regulate appetite. The methods feature administration of a test sample that putatively contains an appetite regulating factor to a recipient mammal. In a preferred embodiment, the recipient mammal exhibits a relatively constant baseline level of chow intake prior to administration of the test sample.

Another aspect of the claimed invention discloses a product having ASF activity. In a preferred embodiment, ASF is secreted by adipose tissue into serum-free, mammalian cell culture medium. This conditioned medium is fractionated using ion exchange chromatography and a 0–0.5M NaCl linear gradient. Eluted fractions having ASF activity are described herein.

A further aspect of the present invention describes a method for reducing food intake in a mammal. Such method features administration of a pharmaceutical composition comprising one or more proteins that correspond to sequences of amino acids described in further detail herein.

A. Methods for Identifying Factors that Regulate Appetite

The present invention provides methods for identification of factors that regulate appetite. These methods can be used to isolate factors that work independently or in concert, and may be used to isolate novel factors that may enhance or diminish appetite.

Appetite suppression factors are assayed using a selected recipient that consumes the same amount of chow each day, by weight, within about a 20% variation. It is preferred that the variation by weight of chow intake not vary by more than 15%, and most preferably, the variation will not exceed 10%. Within the assay of the present invention, an animal is weighed, peripherally injected with a physiologically acceptable buffer (for example, phosphate buffered saline), and fed a pre-weighed, test amount of chow each day at the same time. By peripheral injection, it is meant that the injection is peripheral to the central nervous system. An exemplary peripheral injection includes, but is not limited to, those administered intravenously, subcutaneously, intramuscularly, intranasally, and intraperitoneally. In a preferred embodiment, the injection is administered intraperitoneally. By injecting the animal each day at the same time (±60 minutes), the animal becomes accustomed to daily injection and handling procedures prior to injection of the test sample. After 24 hours, the remaining chow is removed and weighed. The animal is again weighed and test amount chow is replaced. Other factors that are preferably controlled include light exposure and temperature. Injections should be administered at the time of day that is associated with the onset of spontaneous feeding. In a preferred embodiment, the assay animal is a rodent that is preferably exposed to low levels of light (typically 100–200 watts in the room for 12 hours daily), kept at 21°±2° C. and fed in the dark to optimize spontaneous feeding.

In one embodiment, an assay (or recipient) mammal is deficient in the production of a factor that decreases food consumption, but is responsive to exogenously administered factor. Accordingly, the recipient is highly sensitive to the factor if it is present in a test sample. Examples of mammals that are deficient in appetite suppression factors include, for instance, the ob/ob mouse (such as a C57BL/6J ob/ob mouse). Transgenic mice and mice that exhibit a complete absence of gene function, referred to as "knockout mice" (Snouwaert et al., _Science_ 257:3083, 1992), may also be used (Lowell et al., _Nature_ 366:740–742, 1993). However, normal animals have been used successfully in the methods of the present invention, and include, for example, BALB/c mice and KSJ mice. It is preferred that the recipient animals be male.

Once it has been established that an animal's daily chow intake does not vary more than 20%, the animal is weighed, injected with: (1) a test sample; (2) a control buffer used in the preparation of the test sample; or (3) PBS, and presented the test amount of chow. Daily monitoring is done by weighing the animal. After completion of the testing period, the animal is returned to receiving a daily PBS injection and chow consumed is measured, until the animal's daily chow consumption has returned to its baseline. An injection of test sample, buffer or PBS may be given once a day, or multiple injections may be administered to examine prolonged effects on food consumption. The number of injections will be limited by the test animal's tolerance and ability to achieve a baseline feeding profile, as described above. A test sample may be administered once or sequentially over a period of one or more days. If it is desired to measure weight loss, in addition to a decrease in food consumption, then sequential, multiple day injections will be preferred. In a preferred embodiment, an injection is administered once or twice during one 24 h period.

Changes in metabolic factors that regulate appetite and obesity can be measured. For example, changes in glucose and insulin levels can be determined. Blood samples collected at discrete intervals before, during and after administration of a putative ASF are analyzed for changes in the metabolic factors.

Test samples contain a putative appetite suppression factor or factors to be tested in a physiologically acceptable solution. Examples of physiologically acceptable solutions include, but are not limited to, PBS and protein-free cell culture medium that minimally contains a carbon source, a nitrogen source, essential amino acids, vitamins and minerals. Selection of buffers that are physiologically acceptable are well known in the art (see, for example, *Remington's Pharmaceutical Science*, 16th ed., Mack Publishing Company, Easton, Pa. (1982)), which is incorporated herein by reference. Determination of acceptable doses of total protein containing a putative appetite suppression factor is well within the skill of one ordinarily skilled in the art. For example, in mice, doses of conditioned medium that has appetite suppression activity generally are in the range of 0.25 to 1.75 mg protein/g recipient, with preferred doses in a range of 0.5 to 0.75 mg protein/g recipient. One skilled in the art would recognize that, upon purification of a product having appetite suppression activity, the total protein concentration per dose would decrease. In mice, for instance, doses of purified ob protein generally are in the range of 0.01 to 4 μg protein/g recipient/day, with preferred doses in a range of 0.1 to 0.5 μg protein/g recipient/day.

Determination of a decrease in food consumption by the test animal is made by comparing: (1) chow consumption during a 24 hour test period following the time when the animal was injected with the test sample or buffer to (2) chow intake during each 24 hour period preceding, when PBS alone was injected. Additional comparisons between animals given test samples and control animals are performed. The chow intake during the test period may be expressed as a percentage of the mean chow intake from the pre- and post-testing periods (i.e., baseline intake). A significant decrease in food consumption is a reduction to at least 85% of baseline (BL) intake, and preferably at least 75% of baseline.

An in vitro assay to detect an ASF is also advantageous. Preferably, such in vitro assay enables detection and quantitation of biologically active ASF. An in vitro assay can also be used to evaluate changes in metabolic factors regulating appetite and obesity in response to the in vivo administration of a putative ASF. In one embodiment, the in vitro assay is cell-based, and involves either primary or immortalized cultured mammalian cells. Exemplary mammalian cells in this regard include, but are not limited to, islet cells (beta, delta or alpha), adrenal chromaffin cells, neuronal lineage cells, adipocytes and hypothalamic cells. With an islet cell or adrenal chromaffin cell assay, regulation of insulin secretion by a putative ASF can be examined. Alternatively, modulation of triglyceride production, or of glucocorticoid and/or catecholamine production, can be assayed. With neuronal lineage cells, a putative ASF can be tested for hormone-sensitive ion modulation (for instance, dopaminergic and/or serotoninergic effects). With adipocytes, a putative ASF can be examined for autocrine/paracrine effects on the adipocytes, such as 3T3-L1 cells. With hypothalamic cells, binding of a putative ASF to histologic sections of hypothalamus may be determined. Any mammalian cell or cell line that enables detection and quantitation of biologically active ASF may be used to identify a cell line(s) that is an appropriate source for creation of an ASF receptor cDNA library.

B. Appetite Suppression Factor

Microdissected adipose tissue fragments were obtained from db/db mice or, preferably, fa/fa rats. As demonstrated in parabiosis studies, both fa/fa rats and db/db mice are insensitive to a circulating factor(s) that reduces food intake. A current hypothesis proposes that these mice and rats have a defective receptor that is incapable of recognizing this circulating factor. Yet a further hypothesis proposes that these mice and rats produce elevated levels of circulating factor, due to the absence of a functioning receptor and complete feedback loop.

Because adipose tissue excised from fa/fa rats is approximately 10 times greater in mass than that obtained from db/db mice, fa/fa rat adipose tissue is preferred for production of adipose conditioned medium (ACM).

The present invention discloses that appetite suppression factor (ASF) is synthesized and secreted by adipose tissue. When excised, microdissected and minced adipose tissue was cultured short term in serum-free tissue culture medium, the resultant ACM contained one or more factors that suppressed food consumption in recipient mice. When adipose tissue was cultured in the presence of $^{35}$S-methionine, incorporation of $^{35}$S label into trichloroacetic acid (TCA)-insoluble material in the ACM was linear over culturing periods up to 24 h. This incorporation of $^{35}$S label into acid-insoluble material was blocked by incubation of adipose tissue in 0.2 mg/ml cycloheximide. These results are consistent with adipose tissue being more than a mere repository for ASF that has been synthesized and secreted by another tissue. In fact, these data are consistent with adipose tissue's ability to synthesize and secrete ASF de novo.

When concentrated ACM was injected intraperitoneally into BALB/c mice (normal mice), it caused a significant dose-dependent suppression of 24 h chow intake when appropriate assay conditions were used. This appetite down-regulation was not observed following intraperitoneal injection of the following substances: (a) bovine fraction V albumin; (b) excised, microdissected and minced liver tissue conditioned medium; (c) serum obtained from male db/+ mice; (d) BAF3 24-11 cell (thrombopoietin-secreting) conditioned medium; and (e) human fibrinogen. These results are consistent with secretion and synthesis of a specific appetite down-regulating factor by adipose tissue.

ACM prepared using adipose tissue obtained from various anatomic sites yielded comparable appetite suppression activity. More specifically, adipose tissue was dissected from fa/fa rat epididymal, inguinal and dorsal fat pads. When these adipose tissue samples were cultured separately, all conditioned media produced comparable reduction in food intake upon intraperitoneal injection.

Approximately 80% of secreted ASF was present in ACM between 5 and 90 minutes of incubation. After 300 minutes of culturing, an additional 20% increase in ASF was observed. These results were consistent with the appearance of $^{35}$S-labeled acid precipitable material. Moreover, these data provide evidence that ASF is not merely a contaminant residing in adipose tissue.

ASF in ACM was stable to freezing at −70° C. for 2 months; thawing (5 minutes at 37° C.); dilution (activity was recoverable upon reconcentration of 1:10 dilutions of conditioned medium); and concentration by ultrafiltration. However, appetite down-regulating activity was destroyed by heating the ACM at 95° for 5 min. ASF was present in a 66% saturated ammonium sulfate precipitate of ACM, but was eliminated upon exposure to 6M guanidine hydrochloride. Because protease-treated ACM could not be safely administered to mice, the in vivo effect of protease treatment of ACM was not determined. These observations provide evidence that the active factor(s) in ACM is a protein.

ACM was fractionated using membrane ultrafiltration and membranes that retain various sizes of molecules. More specifically, adipose tissue was excised from 3 Zucker rats, and the resultant ACMs were pooled. The pooled material was concentrated using a 1 kD cut-off ultrafiltration membrane, and stored in 1 ml aliquots at −70° C. The protein concentration in this concentrated ACM was calculated to be about 13 mg/ml. In the mouse bioassay, this preparation reduced chow intake to 44±11% of baseline. Subsequently, five 1 ml aliquots were thawed and diluted 1:10 in PBS. The dilute ACM was fractionated using a Centriprep 3, 10, or 30, or a Centricon 100 apparatus. The ACM retentates had protein concentrations of 5.5, 7.0, 6.4 and 6.0 mg/ml, respectively. When retentates were tested in the mouse bioassay, chow intake was determined to be 97, 43, 86 and 67% BL, respectively.

The appetite suppression that was obtained using fractionated ACM retentate from the Centriprep 30 column was similar to that of the unfractionated ACM, which contained about twice the concentration of protein. More specifically, administration of equal volumes of preparations provides the following ratios: unfractionated, concentrated ACM=44% BL/13 mg/ml protein; fractionated, >30 kD, concentrated ACM=43% BL/7.0 mg/ml. This fractionated composition may also be termed "isolated", meaning that the fractionated composition is found in a condition other than its original environment, such as unconcentrated and unfractionated conditioned medium. Alternatively, Zucker rat ACM has been subjected to HPLC and fractionated. The HPLC fractions represent "isolated" preparations, also. In fact, HPLC-isolated compositions exhibited less complexity (i.e., more isolation) than ultrafiltration retentates.

The ASF secreted into ACM was not tumor necrosis factor alpha (TNF-α), a known anorexic agent produced by adipose tissue. The concentration of TNF-α in ACM, as measured by an L929 cell cytotoxicity assay (Aggarwal et al., *J. Biol. Chem.* 260: 2345, 1985), was over 100-fold less than the concentration of purified recombinant mouse TNF-α required to suppress feeding in the assay of the present invention.

To demonstrate that the ASF present in ACM is capable of acting on the central nervous system (CNS), adipose tissue was excised from Long-Evans rats (normal outbred rats) that had been gavage overfed to produce obesity and a complete cessation of spontaneous chow intake. When this Long-Evans ACM was injected intracerebrally into recipient rats, a significant feeding suppression was observed, as compared to recipients that were injected with unconditioned medium alone. The central effective dose was 1000-fold less than the peripheral effective dose of Long-Evans ACM, consistent with a central locus of ASF action.

ASF may increase CNS responsiveness to gastrointestinal meal termination signals, resulting in reduced average meal size or frequency. The hyperphagia of the ob/ob mouse may generate a high level of gastrointestinal feedback to the CNS, therefore ob/ob mice may be unusually sensitive to exogenously administered ASF. In fact, intraperitoneal injection of ACM resulted in greater feeding suppression in ob/ob mouse recipients than in BALB/c recipient mice. Moreover, the duration of feeding suppression in ob/ob recipients was about 3 days, as compared to about 1 day for BALB/c recipients.

Because of the enhanced responsiveness of ob/ob recipients to injections of ACM, ob/ob recipients are preferred recipients for injection of test samples that putatively contain ASF. In a preferred embodiment, an ob/ob recipient is injected intraperitoneally with a test sample. When ACM is the test sample, a single 1 ml injection of medium that has been conditioned for 3–5 h, then concentrated 20× by ultrafiltration through a 1000 Dalton molecular weight cut-off membrane, is preferred.

The apparent hypersensitivity of ob/ob mice to injection of ACM did not result from a non-specific toxic effect. When db/db mice were injected intraperitoneally at a dose of 0.40 mg/g, the db/db recipients' 24 h food intake was reduced to 89% of baseline, whereas the ob/ob recipients' 24 h food intake was reduced to 58% of baseline. These data are inconsistent with non-specific toxicity of the ACM, which would have affected ob/ob and db/db recipients equally. However, these results are consistent with the preciously reported insensitivity of db/db mice to parabiotic satiety factor (Coleman and Hummel, *Am. J. Physiol.* 217: 1298, 1969; Coleman, *Diabetologia* 9:294, 1973).

A two bottle conditioned taste aversion test, a standard paradigm for distinguishing physiological regulators of feeding from substances that reduce feeding through the induction of malaise (Spear et al., *Ann. N.Y. Acad. Sci.* 443:42, 1985), confirmed that ACM acted as a specific regulator of feeding. Taste aversion could not be produced in ob/ob mice by pairing intraperitoneal injections of ACM with the presentation of a novel flavor, but could be produced by pairing lithium chloride, an established nauseant (Nachman and Ashe, *Physiol. Behav.* 10:73, 1973), with a novel flavor.

Medium conditioned with adipose tissue excised from ob/ob mice exhibited significantly lower appetite suppression activity than media conditioned with adipose tissue excised from other strains of rodents. These data are consistent with previously reported parabiosis results, and provide further evidence that ACM from donors other than ob/ob mice contains a specific active factor.

A single daily injection of fa/fa rat ACM produced a sustained reduction in chow intake and progressive weight loss when administered to ob/ob recipients over the course of 10 days, as compared to ob/ob recipients that received injections of PBS. This weight loss was attributable exclusively to reduced caloric (i.e., chow) intake as shown by the comparable rate of weight loss in pair fed animals. These data were inconsistent with an increased energy expenditure as a result of physiological or pathophysiological effects of ACM.

In order to further characterize ACM, a large pool of fa/fa ACM was prepared. When an aliquot of this large pool was concentrated by ultrafiltration, no appetite down-regulating activity was observed upon injection into ob/ob recipients. The concentrated material was applied to an ion exchange column and eluted with a salt gradient. The most significant ASF activity in the resultant partially purified fractions eluted at a concentration of 0.1–0.5M NaCl, with fractions eluted at 0.1–0.25M NaCl, at 0.25–0.38M NaCl, and at 0.38–0.5M NaCl preferred.

C. Methods for Reducing Food Consumption

The sequence of a cDNA clone encoding a representative mouse appetite suppression factor (mouse ob protein) is shown in SEQ ID NO:1, and the corresponding amino acid sequence is shown in SEQ ID NO:2. The sequences of the human DNA and protein are shown in SEQ ID NO:3 and SEQ ID NO:4, respectively. Those skilled in the art will recognize that the sequences shown in SEQ ID NOS. 1, 2, 3 and 4 correspond to single alleles of the murine and human ob genes, and that allelic variation is expected to exist. Allelic variants of the DNA sequences shown in SEQ ID NO:1 and NO:3, including those containing silent mutations and those in which mutations result in amino acid sequence changes, are useful within the present invention, as are proteins which are allelic variants of SEQ ID NO:2 and NO:4.

An exemplary allelic variant of the mouse nucleic acid and protein of SEQ ID NO:1 and NO:2 is shown in SEQ ID NO:5 and SEQ ID NO:6. Only the mature protein and its coding sequence are shown. In this variant, the Gln residue at position 49 of SEQ ID NO:2 is not present.

The DNA molecule shown in SEQ ID NO:1 was cloned by polymerase chain reaction (PCR; see Mullis et al., U.S. Pat. No. 4,683,195; Mullis, U.S. Pat. No. 4,683,202) using primers designed from the sequence of the mouse obese gene (Zhang et al., *Nature* 372:425–432, 1994) and cDNA made from db/db mouse adipose tissue mRNA. A second round of PCR was used to add restriction sites at the ends of the DNA to facilitate subsequent manipulations. The mouse DNA was used to probe a human adipose tissue cDNA library (obtained from Clontech, Palo Alto, Calif.), and the DNA molecule shown in SEQ ID NO:3 was isolated.

The appetite suppression factor DNA and amino acid sequences disclosed herein are useful tools for preparing isolated polynucleotide molecules encoding appetite suppression factors from other species ("species homologs"), in particular other mammalian species. DNA molecules, including complementary DNA (cDNA) and genomic DNA, can be cloned by conventional techniques using readily available reagents. Methods for using sequence information from a first species to clone a corresponding polynucleotide sequence from a second species are well known in the art. See, in general, Ausubel et al., eds., *Current Protocols in Molecular Biology*, John Wiley and Sons, Inc., NY, 1987. Suitable techniques in this regard include polymerase chain reaction, hybridization to labeled probes (see, e.g., Sambrook et al., eds., *Molecular Cloning: A Laboratory Manual*, 2nd ed., Cold Spring Harbor Laboratory, 1989) and expression cloning using antibody probes or soluble receptors (e.g., Young and Davis, *Proc. Natl. Acad. Sci. USA* 80:1194–1198, 1983). DNA molecules encoding ASF proteins are generally at least 60%, preferably at least 80%, and may be 90–95% or more identical in sequence to SEQ ID NO: 1, SEQ ID NO:3, or their allelic variants.

Analysis of the amino acid sequences shown in SEQ ID NO:2 and SEQ ID NO:4 indicated that each protein included an amino-terminal signal peptide of 21 amino acid residues. The mature proteins thus begin with amino acid residue 22 (Val) of SEQ ID NO:2 and SEQ ID NO:4.

For use within the present invention, it is preferred to prepare the representative appetite suppression factor as a recombinant protein, that is by introducing DNA encoding the protein into a host cell and culturing the cell so that the DNA is expressed and the protein can be recovered. DNA molecules can be introduced into cells according to conventional procedures. In general, a DNA molecule encoding an appetite suppression factor is inserted into an expression vector, where it is operably linked to additional DNA segments that provide for its transcription. Such additional segments include promoter and terminator sequences. An expression vector may also include one or more origins of replication, one or more selectable markers, an enhancer, a polyadenylation signal, etc. Expression vectors are generally derived from plasmid or viral DNA, or may contain elements of both. The term "operably linked" indicates that the DNA segments are arranged so that they function in concert for their intended purposes, e.g., transcription initiates in the promoter and proceeds through the coding segment to the terminator. Methods for introducing DNA into prokaryotic and eukaryotic cells and culturing the cells are well known in the art. Suitable host cells include prokaryotic cells (e.g., bacteria of the genera Escherichia and Bacillus), unicellular microorganisms (e.g., yeasts of the genera Saccharomyces, Pichia, Schizosaccharomyces and Kluyveromyces), and cells from multicellular organisms (e.g., mammalian cells, including BHK, CHO and COS cell lines; insect cells; avian cells; and plant cells). See, for example, Kawasaki, U.S. Pat. No. 4,599,311; Kingsman et al., U.S. Pat. No. 4,615,974; Bitter, U.S. Pat. No. 4,977,092; Welch et al., U.S. Pat. No. 5,037,043; Murray et al., U.S. Pat. No. 4,766,073; Wigler et al., *Cell* 14:725, 1978; Corsaro and Pearson, *Somatic Cell Genetics* 7:603, 1981: Graham and Van der Eb, *Virology* 52:456, 1973; Neumann et al., *EMBO J.* 1:841–845, 1982; Ausubel et al., eds., *Current Protocols in Molecular Biology*, John Wiley and Sons, Inc., NY, 1987; Hawley-Nelson et al., *Focus* 15:73–79, 1993; Hagen et al., U.S. Pat. No. 4,784,950; Palmiter et al., U.S. Pat. No. 4,579,821; Ringold, U.S. Pat. No. 4,656,134; Foster et al., U.S. Pat. No. 4,959,318; Cregg, U.S. Pat. No. 4,882,279; Stroman et al., U.S. Pat. No. 4,879,231; McKnight et al., U.S. Pat. No. 4,935,349; Guarino et al., U.S. Pat. No. 5,162,222; Bang et al., U.S. Pat. No. 4,775,624; WIPO publication WO 94/06463; Sinkar et al., *J. Biosci. (Bangalore)* 11:47–58, 1987; Lambowitz, U.S. Pat. No. 4,486,533; Sambrook et al., eds., *Molecular Cloning: A Laboratory Manual*, 2nd ed., Cold Spring Harbor Laboratory, 1989; Goeddel et al., U.S. Pat. No. 4,766,075; and Baird et al., U.S. Pat. No. 5,155,214, which are incorporated herein by reference in their entirety. Suitable expression vectors and host cells are widely available from commercial suppliers.

Secretion of the ob protein can be enhanced by substituting a synthesized secretory peptide, for example, a secretory peptide derived from that of human tissue-type plasminogen activator (t-PA) for the native ob signal peptide. t-PA secretory peptides are known in the literature, see, for example, Rickles et al., *J. Biol. Chem.* 263:1563–1560, 1988 and Feng et al., *J. Biol. Chem.* 265:2022–2027, 1990.

The expressed recombinant protein is isolated from the host cells using conventional purification methods, such as affinity chromatography, ion exchange chromatography, reverse-phase high performance liquid chromatography and size exclusion chromatography. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

The present invention provides an ob protein preparation in a homogeneous form. The substantially purified ob protein of the present invention was prepared using affinity chromatography (about 85% pure) and HPLC, and is characterized by an $M_r$=16,482±500 daltons, as determined by mass spectroscopy. This purified protein exhibits migration differences on SDS-polyacrylamide gel electrophoresis under non-denaturing versus denaturing conditions, confirming the presence of a disulfide bond. The ob protein of the present invention is provided at least 90% pure with respect to other contaminating proteins, as determined by HPLC analysis. The purified ob protein caused appetite suppression in the mouse bioassay (81±3% BL at a dose of 13–17 $\mu$m per mouse recipient.

Purification of ob protein has also been achieved using a combination of chromatography methods, including affinity chromatography, Q-Fast Flow Sepharose, MonoQ resin, FPLC, phenyl Sepharose, hydroxyapatite, Mono S and/or S-Sepharose. For some preparations, it is preferable to use borate-based buffers, preferably about 1–100 mM borate, and more preferably 10 mM borate, pH=7.4. In another preferred embodiment, it is preferred to prepare substantially pure preparations of ob protein in the presence of trace metals. Suitable trace metals in this regard include $ZnCl_2$, $CaCl_2$, $Na_2MoO_4$, $CuSO_4$, and $FeCl_3$. One of skill in the art will recognize that other divalent and trivalent cations may also be suitable for this purpose. In a preferred embodiment, one or more of each of the trace metals is present at a concentration from about 1 to 100 $\mu$M. It is preferred that the type and concentrations of metal(s) added enhance the biological activity of the ob protein preparation, as compared to a preparation that does not contain trace metals.

It is convenient to express the appetite suppression factor as a fusion with an affinity "tag", such as a polypeptide for which an antibody or other specific binding agent is available. A preferred such affinity tag is a polyhistidine tail, which permits purification of the fusion protein on immobilized nickel (Houchuli et al., *Bio/Technol.* 6: 1321–1325, 1988). In prokaryotic expression systems, a maltose binding protein (MBP) fusion may be advantageously used as an affinity tag. If the protein is to be recovered from the cytoplasm or periplasm of the host cells, the cells are first disrupted, and a crude extract containing the protein is recovered and subjected to further purification steps. Secreted protein is recovered from cell-conditioned media, preferably after concentration of the conditioned media. Selection of particular fractionation steps and the sequence of those steps will be based in part on the type of host cell and the expression system (secretory vs. non-secretory) chosen. Such determinations are within the level of ordinary skill in the art.

The expressed recombinant ASF protein is useful for production of antisera and purified antibodies. For instance, recombinant ASF (crude, partially purified or purified to homogeneity) may be advantageously injected into a subject mammal (preferably a mouse, rat or rabbit) using methods known in the art to lead to production of antibodies in the subject mammal. At appropriate intervals, the animals are bled, and polyclonal antiserum is obtained. Antibodies monospescific for ASF may be prepared by passing this polyclonal antiserum over an insolubilized matrix having purified ASF bound thereto, then eluting the bound antibodies. Alternatively, monoclonal antibodies that bind ASF may be prepared using standard hybridoma technologies. In addition, recombinant antibodies may be prepared using known techniques. The term "antibody" as used herein includes, but is not limited to, intact antibodies, proteolytic fragments of antibodies, Fv's, complementarity determining regions, single chain antibodies, epitope-binding domains of protein or non-protein origin, and the like.

Anti-ASF antibodies have been advantageously used in a variety of protein detection and purification methods. An exemplary anti-ASF antibody is anti-ob antibody. Such antibodies are useful for radioimmunoprecipitation, immunoprecipitation, Western blotting, antibody affinity chromatography, antigen depletion and the like. For some studies, the immunogen (e.g., ob protein) preparation was either untreated or denatured prior to immunization. Because certain protein analytical techniques involve denaturing a protein preparation, such native/denatured "paired" production of antibodies enabled more precise analysis of antigen.

For pharmaceutical use, appetite suppression factors are formulated for parenteral (e.g., intravenous, subcutaneous, intramuscular, intraperitoneal, intranasal or transdermal) or enteral (e.g., oral or rectal) delivery according to conventional methods. Intravenous administration will be by a series of injections or by continuous infusion over an extended period. Administration by injection or other routes of discreetly spaced administration will generally be performed at intervals ranging from weekly to once to three times daily. Treatment will continue until the desired body weight is reached, after which maintenance doses may be administered as necessary to regulate food consumption and body weight within the desired range. In general, pharmaceutical formulations will include an appetite suppression factor in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, lubricants, fillers, stabilizers, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Pharmaceutical compositions for use within the present invention can be in the form of sterile, non-pyrogenic liquid solutions or suspensions, coated capsules, suppositories, lyophilized powders, transdermal patches or other forms known in the art. Therapeutic doses will generally be in the range of 0.1 $\mu$g/kg to 1 mg/kg of patient weight per day, preferably 1–100 $\mu$g/kg per day, with the exact dose determined by the clinician according to accepted standards, taking into account the nature and severity of the condition to be treated, patient traits, etc. Determination of dose is within the level of ordinary skill in the art. Initial dose determinations can be made by extrapolation from animal models according to standard principles, taking into consideration route of administration and pharmacokinetic factors such as rate of absorption, distribution, biotransformation, bioavailability and rate of excretion. See, for example, Goodman and Gilman, eds., *The Pharmacological Basis of Therapeutics*, Fifth Edition, MacMillan Publishing Co., Inc., New York, 1975.

The ob protein, a representative appetite suppression factor, is a useful tool for the study of appetite control. For example, the protein can be used to design a probe for cloning DNA encoding its cellular receptor. Methods for cloning cellular receptors are known in the art. In a preferred method, mammalian cells (e.g., BHK 570 cells; ATCC CRL 10314) are transfected with a cDNA library prepared from ventromedial hypothalamus tissue. The transfectants are plated, and labeled appetite suppression factor is applied to the cell layer. Binding of ob protein (appetite suppression factor) is indicative of receptor expression.

In an alternative method, degenerate primers are designed from sequences of known members of the cytokine receptor superfamily, based on the putative structural homology of ligands for the receptors of this family. Using pattern recognition (Cohen et al., *Biochem.* 25:266–75, 1986) and neural network (Kneller et al., *J. Mol. Biol.* 214:171–82, 1990) software for the production of secondary structure, the ob gene product was predicted to fold into a four alpha-helix bundle. This helical structure prediction was used as a guide in the generation of a multiple alignment with other helical cytokines (Buzan, *Immunology Today* 11: 350–54, 1990; and Gribskov et al., *PNAS USA* 84: 4355–58, 1987). The multiple alignment demonstrated that ob protein has similarity to the helical cytokine structure class. Additional evidence of the possible relatedness of ob protein to the helical cytokine structure class was provided by the two forms of ob cDNA (+Gln and −Gln). These two forms may be caused by slippage at a splice acceptor sequence, indicating the location of a exon-intron boundary (Zhang et al., ibid). With respect to the multiple alignment, the location of the exon-intron boundary of ob was determined to be coincident with an exon-intron boundary in interleukin-3 and GM-CSF, and is within two residues of exon-intron boundaries in interleukin-2 and interleukin-6.

For cloning an ASF receptor, genomic DNA is amplified, and overlapping, complementary clones are extended and amplified using primers specific for engineered 5' and 3' tails on the template DNA. DNA molecules encoding a receptor for ASF are then cloned through the application of conventional techniques. Such molecules are then expressed in engineered host cells to produce recombinant ASF receptor. The receptor, in cell-bound or cell-free form, is used to screen compounds for ASF agonist or antagonist activity. Screening methods of this type are known in the art (see, for example, Hendry et al., *J. Immunological Methods* 35:285–296, 1980; and Lam et al., *Nature* 354:82–84, 1991). In general, a test sample is assayed for the ability to bind to the receptor and, in a cellular system, produce or inhibit a biological response in the target cell. Compounds identified in this manner may find utility in the treatment of a variety of eating disorders, or may be lead compounds for further development of therapeutic agents. Assays of the type disclosed above are, of course, useful within such further development.

The invention is further illustrated by the following non-limiting examples.

EXAMPLES

Example 1. Methods for Establishing Recipient Test Animals

Nine 6–8 week-old male, C57BL/6J-ob/ob (non-diabetic) mice (Jackson Laboratories, Bar Harbor, Me.) were isolated to separate cages with one animal per cage. The weight of the mice ranged from 38 to 47 grams. The mice were presented with preweighed quantities of chow in the range of 14–18 grams of standard rodent chow blocks (Teklad, Madison, Wis.), water and given a 1 ml intraperitoneal injection of PBS at 0930–1030 hours. The lights were turned off until 2230 hours, reversing the normal light cycle.

Twenty-four hours later, the uneaten chow blocks were removed and weighed. Each animal was removed from its cage, weighed and injected with 1 ml of PBS, intraperitoneally. New chow blocks were weighed and placed in each cage, and lights were turned off. This process was repeated for five days until all nine mice were identified as having consumed the same amount of chow, within a 10% deviation, for two feeding cycles. Table 1 shows the net chow weight consumed by each animal to establish the baseline. Day 1 begins feeding program.

TABLE 1

| | Day: | | | | | |
|---|---|---|---|---|---|---|
| | 2 | 3 | 4 | 5 | 6 | 7 |
| mouse # | grams of consumed food | | | | | |
| 87 | 5.9 | 6.6 | 7.4 | 6.8 | 6.9 | 5.7 |
| 84 | 4.5 | 5.3 | 6.2 | 6.7 | 6.5 | 7.2 |
| 78 | 5.7 | 6.4 | 7.8 | 8.5 | 6.7 | 7.1 |
| 74 | 5.7 | 6.4 | 7.4 | 6.3 | 6.9 | 7.5 |
| 86 | 5.6 | 6.0 | 6.6 | 7.3 | 6.6 | 6.4 |

TABLE 1-continued

| | Day: | | | | | |
|---|---|---|---|---|---|---|
| | 2 | 3 | 4 | 5 | 6 | 7 |
| mouse # | grams of consumed food | | | | | |
| 83 | 4.9 | 5.0 | 5.7 | 5.8 | 5.2 | 5.4 |
| 79 | 5.9 | 6.3 | 6.6 | 6.9 | 6.2 | 6.8 |
| 77 | 5.4 | 6.6 | 5.7 | 5.0 | 6.5 | 6.7 |
| 88 | 4.8 | 4.7 | 6.0 | 5.8 | 6.0 | 6.1 |

By day 7, it was established that each mouse had acceptable variation in food consumption, compared to consumption on day 6, and the animals were administered a single injection of test sample or control buffer on day 7.

Example 2: Adipose Conditioned Medium

A. Preparation of Adipose Conditioned Medium

Epididymal, inguinal, dorsal and retroperitoneal adipose tissue pads were removed from 12–14 week old non-fasted male fa/fa (Zucker) rats (Harlan Sprague Dawley Co., Madison, Wis.) under methophane anesthesia, placed into room temperature Dulbecco's Modified Eagle's medium (DMEM) containing 4.5 g/l glucose , 2 mM L-glutamine and 20 mM HEPES (Sigma, St. Louis, Mo.), and dissected immediately after collection into 10–15 mg fragments using sharp scissors. Microdissected tissue fragments were washed once in medium and incubated in 150 mm culture dishes (American Scientific Products, Chicago, Ill.) for 3–5 h at 37° C. and 5% $CO_2$ atmosphere. Approximately 2.5 ml of medium was used per gram of tissue. Following incubation, fat was removed by centrifugation at 2200 g, and the aqueous layer was filtered through a 0.2 $\mu$m membrane (American Scientific Products). The filtrate was concentrated 20 fold using a 1 kDa cutoff membrane and a sterile 76 mm pressure cell (YM-1 membrane, Amicon, Chicago, Ill.) to a volume of 3–5 ml per rat. The final protein concentration was determined using a Pierce BCA assay (Pierce, Rockford, Ill.), according to the manufacturer's specifications.

B. Adipose Tissue Synthesizes and Secretes ASF

Male, non-fasted db/db adipose tissue (about 2 g) was microdissected and placed in medium, as described in 2.A., above, containing $10^{-7}$M insulin. The adipose tissue was washed once with unlabeled medium, then resuspended in 4 ml of medium containing 5 $\mu$l EXRE$^{35}$S$^{35}$S® Protein Labeling Kit (NEN, Boston, Mass.; a mixture of $^{35}$S-methionine and $^{35}$S-cysteine; also designated "$^{35}$S-EXPRESS", herein). The adipose tissue was incubated in this medium for 210 min, and every 30 min a 200 $\mu$l sample was removed. To each 200 $\mu$l sample was added 15 $\mu$l fetal bovine serum (FBS) as a carrier and 200 $\mu$l cold 40% trichloroacetic acid (TCA). This mixture was held on ice for 1 h, then filtered through a Whatman GFA glass fiber filter. The filter was washed with 10 ml 20% TCA, and the filters were dried and counted.

The TCA-insoluble material derived from the $^{35}$S-labeled conditioned medium exhibited a linear and progressive incorporation of radioactivity over the full time course of the experiment. These results indicate that the adipose tissue is synthesizing new protein during incubation in the culture medium. When the time course of this experiment was extended to 20 h, linear incorporation of $^{35}$S into TCA insoluble material was observed.

To determine the effect of cycloheximide on incorporation of $^{35}$S label into TCA-insoluble material, adipose tissue was treated as above, but duplicate preparations were prepared.

To one of the duplicates, cycloheximide (0.2 mg/ml) was added at time 0, and the experiment was run for 480 min. In the duplicate preparations that included cycloheximide, a noticeable decrease in $^{35}S$ incorporation into TCA-insoluble material was noted.

C. Radioimmunoprecipitation of db/db Mouse Adipose Conditioned Medium (ACM)

An ACM radiolabeled protein preparation was obtained as follows. Retroperitoneal, inguinal, epididymal and dorsal fat pads were harvested from a 41 g female db/db C57BL/6J (Jackson Labs) mouse (8 weeks of age). The fat (7.8 g) was processed as described in 2.A., above, except that the fat was microdissected in PBS, and washed three times with 40 ml of fresh PBS (each wash). The fat was then suspended in 20 ml of labeling medium (DMEM minus methionine and cysteine, and containing L-glutamine (0.29 mg/ml), penicillin (0.05 mg/ml), streptomycin (0.05 mg/ml), neomycin (0.01 mg/ml), sodium pyruvate (0.1 mg/ml), 10 mM HEPES, pH 7.0, insulin (5 µg/ml), and $^{35}S$-EXPRESS (10 µCi/ml)) in a 150 mm tissue culture dish. The fat was radiolabeled for 5.5 h. The medium was removed from under the fat, sterile filtered with a 0.2 µm filter, and concentrated using a Centriprep-3 (Amicon) device. Radiolabeled medium (15 ml) was concentrated to 800 µl at 4° C.

D. Detection of ob Protein in ACM

Concentrated ACM (200 µl) was mixed with 5 µl or with 25 µl polyclonal anti-ob antibody (2 mg/ml; raised against denatured MBP::ob fusion protein, as described in Example 10.B., infra). These mixtures were incubated on ice for approximately 3 h.

A PANSORBIN (Calbiochem, La Jolla, Calif.) stock solution was fully resuspended and two 1 ml aliquots of PANSORBIN cells were withdrawn. These aliquots were microfuged at ≈4,000 RPM at 4° C. The pellets were resuspended in 50 mM Tris, pH 7.4, containing 150 mM NaCl, 5 mM EDTA and 0.5% NP-40. This mixture was recentrifued and resuspended in the same solution with NP-40 at 0.05%, instead of 0.5%. Each PANSORBIN aliquot (100 µl) so prepared was mixed with an ACM/antibody mixture (either 5 µl or 25 µl Ab), and incubated for 15 min at room temperature. After this incubation, the PANSORBIN/ACM/antibody mixtures were centrifuged at 4° C., 10,000 RPM for 2 min. The supernatant was removed, and the pellet was resuspended in 30 µl of 1× SDS-PAGE sample loading buffer (63 mM Tris, pH 6.8, containing 10% (v/v) glycerol, 2% (w/v) SDS, 5% (v/v) β-mercaptoethanol and 0.0125% (w/v) bromophenol blue). The SDS-PAGE samples were boiled for 5 min, chilled, and loaded onto a Daiichi 10–20% glycine PAGE multigel (Integrated Separation Systems, Natick, Mass.), along with MULTIMARK molecular weight markers (Novex, San Diego, Calif.; multicolored size markers).

The gel was electrophoresed at constant voltage (125V) until the dye front was approximately 1 cm from the bottom of the gel. The gel was fixed in methanol/acetic acid (40%/10%) for 30 min at room temperature, then soaked with AMPLIFY (Amersham) for an additional 30 min. The gel was then dried down onto blotting paper, exposed to phosphor plates for 8 h, and analyzed using a PHOSPHO-IMAGER (Molecular Dynamics, Sunnyvale, Calif.). Subsequently, the gel was also exposed to X-ray film overnight.

A discrete band migrating at the predicted molecular weight of ob protein was observed. This result evidences that ob protein is present in ACM.

E. Detection of ob mRNA mRNA levels of ob in normal rats that had either been fasted or fed was examined. Adipose tissue from 16 week-old male Sprague Dawley rats (Harlan Sprague Dawley Co., Madison, Wis.) was collected from the following groups:

1) rats fasted for 48 hours
2) rats fasted for 72 hours
3) rats fasted for 48 hours and refed for 24 hours
4) rats fed ad libitum The RNA was isolated according the the method of Chomczynski et al., Anal. Biochem. 162:156–159, 1987. Northern analysis was done using 11 µg of RNA from each group electrophoresed on 1% agarose gels and transferred to nitrocellulose. The nitrocellulose filters were probed using $^{32}P$-labeled mouse ob cDNA (SEQ ID NO:1). Results, showed that ob mRNA levels observed in adipose tissue from the refed (group 3) and ad libitum fed (group 4) donor animals were approximately twice the levels observed from the animals fasted for 48 hours (group 1) and 72 hours (group 2).

Example 3: Adipose Conditioned Medium Suppresses Food Intake in ob/ob Recipient Mice Male BALB/c mice received two daily intraperitoneal injections (0.5 ml) of concentrated fa/fa rat adipose conditioned medium (see Example 2.A., above) having a protein concentration of 25–35 mg/ml. Comparable male BALB/c mice received two daily intraperitoneal injections of one of the following control preparations:

(a) bovine fraction V albumin (Sigma) in PBS at a concentration of 28.6 mg/ml or 14.3 mg/ml;

(b) liver conditioned medium at a concentration of 45.4 mg/ml or 22.7 mg/ml, obtained by culturing microdissected liver tissue excised from a 500 g male Sprague-Dawley rat under the same conditions as described for adipose conditioned medium (see Example 2, above);

(c) serum obtained by orbital bleeding of male db/+ mice (Jackson Laboratory), administered as a 0.5 ml intraperitoneal dose;

(d) BAF3 24-11 (an IL-3-dependent cell line that expresses mouse thrombopoietin) conditioned medium, wherein the medium [per 500 ml of F-DV (an equal mixture of D-MEM and Ham's F-12 media), the following were added: 50 µl transferring (10 mg/ml); 500 µl insulin (5 mg/ml); 250 µl selenium (4 µg/ml); 5 ml fetuin (1 mg/ml); 5 ml sodium pyruvate; 5 ml L-glutamine (29 mg/ml); and 12.5 ml 25 mM HEPES] tested at 6.25 mg/ml; or (e) human fibrinogen in PBS at a concentration of 28.3 mg/ml or 14.15 mg/ml.

As shown in FIG. 1, the fa/fa adipose conditioned medium produced a dose-related suppression of 24 h chow intake. The maximal exceeded any suppression observed in recipients that received injection of a control preparation.

Example 4: Adipose Tissue Excised in Overfed Rats

Retroperitoneal adipose tissue was collected under chloral hydrate/pentobarbital anesthesia from overnight-fasted Long-Evans rats that had been chronically overfed to produce obesity, as described by B. E. Wilson et al., Am. J. Physiol. 259: R1148, 1990. Two to four grams of adipose tissue were microdissected and incubated for 4 h at 37° C. in 10 ml of tissue culture Medium 199 plus 15 mM HEPES and 1 µg/ml leupeptin. Conditioned medium was concentrated by ultrafiltration (1 kD cutoff), and final protein concentration was determined by the method of Bradford (Anal. Biochem., 72:248–54, 1976).

An aliquot of this Long-Evans adipose conditioned medium was injected into the third cerebral ventricle of rats trained to consume a test meal. More specifically, stainless steel 22 gauge cannulas were stereotaxically placed into the third ventricles of six 300 g male Long-Evans rats that were subsequently trained to consume a 2 h test meal of powdered chow at the onset of darkness. Chow was also presented for 6 h at the end of the dark phase to assure normal 24 h caloric intake and growth. Cannula function was confirmed by a positive drinking response to a 100 ng bolus injection of angiotensin II. All injections were given immediately prior to the beginning of the dark phase, and chow was weighed 2 h later.

A 15 µl aliquot of concentrated Long-Evans ACM (containing 50, 60, 170, 290 or 350 µg protein) was injected intracerebroventricularly into a cannulated recipient rat (described above). Data are expressed as a percentage of baseline (% BL), which was the mean 2 h chow intake following a 15 µl injection of unconditioned Medium 199 on the day preceding and the day following administration of adipose conditioned medium. Points represent the mean±SE determined using 6 rats per group for each protein amount injected. The line represents the best fit of logarithmic function to the data set ($r^2+0.734$, $p<0.05$).

Figure 2:
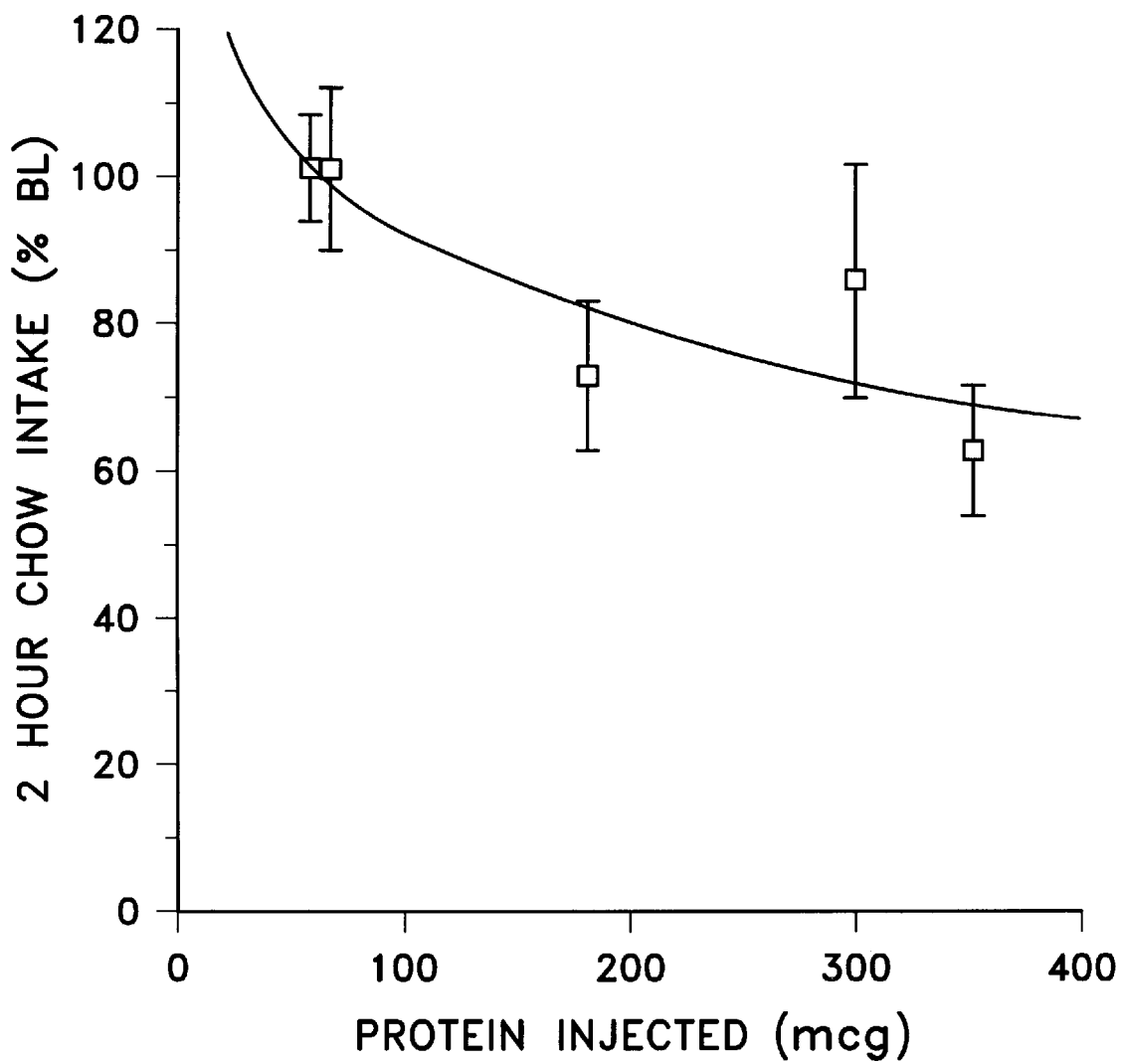
FIG. 2 shows a dose-dependent feeding suppression upon intracerebroventricular (central) injection of adipose conditioned medium that was prepared using adipose tissue from normal rats that had been gavage overfed.

The recipients of adipose conditioned medium exhibited a significant feeding suppression, as compared to baseline food intake (FIG. 2). The centrally effective Long-Evans adipose conditioned medium protein dose of 0.35 mg in a 300 g recipient rat (e.g., 1.17 mg/kg) was about 1000-fold less than the peripherally effective dose of 30 mg in a 25 g mouse (e.g., 1200 mg/kg). This central-to-peripheral dose ratio, which is expected on the basis of the blood-brain barrier and dilution of an endocrine factor in the circulation, was consistent with a central locus of ASF action.

Example 5: Comparison of Feeding Suppression in Various Mouse Strains

The effect of fa/fa adipose conditioned medium on chow intake of ob/ob mice, db/db mice and BALB/c mice was determined. ob/ob mice of both sexes were obtained from Jackson Laboratories at 6–8 weeks of age and studied at a body weight of 45–55 g.

Figure 3:
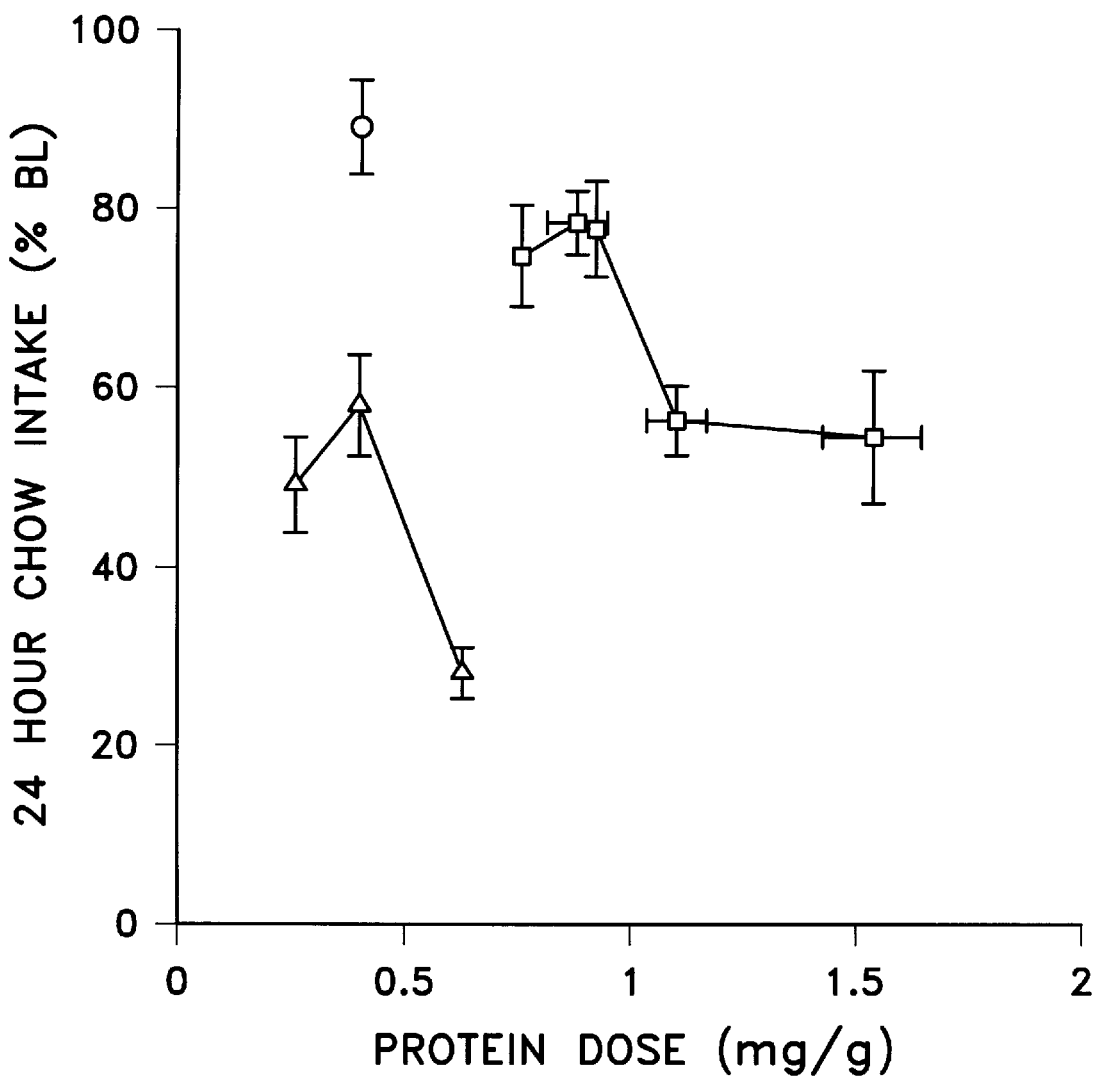
FIG. 3 represents food consumption following administration of various doses of fa/fa adipose conditioned medium to normal and mutant mouse recipient strains. Recipients: ob/ob (triangles); db/db (circles); Balb/c (squares).

Briefly, a recipient mouse was administered two daily intraperitoneal injections of fa/fa adipose conditioned medium at a dose indicated in FIG. 3, and 24 h chow intake was measured (FIG. 3). ob/ob recipients are represented by triangles; db/db mice by circles; and BALB/c mice by squares. Points represent the mean±SE using 2–5 mice per group for each protein dose injected. Greater feeding suppression was observed in ob/ob mice than in db/db or BALB/c mice.

Five db/db mice received a 0.40 mg/g intraperitoneal dose of ACM. This dose was matched to the 0.40 mg/g median dose administered to one of the three groups of ob/ob recipients. The db/db recipients displayed a 24 h food intake that was 89±5.1% of baseline level, as compared to the three ob/ob mice that showed a 24 h food intake that was 58±5.5% of baseline level (p=0.01).

Since the injected ACM diminished food intake in ob/ob mice (which are believed to have a deficiency in production of satiety factor), but not in db/db mice (which are believed to be insensitive to satiety factor), these results evidence a specific appetite regulating activity. Accordingly, these data rule out the possibility that ACM exerted a non-specific toxic effect, which would have affected both strains equally.

Figure 4:
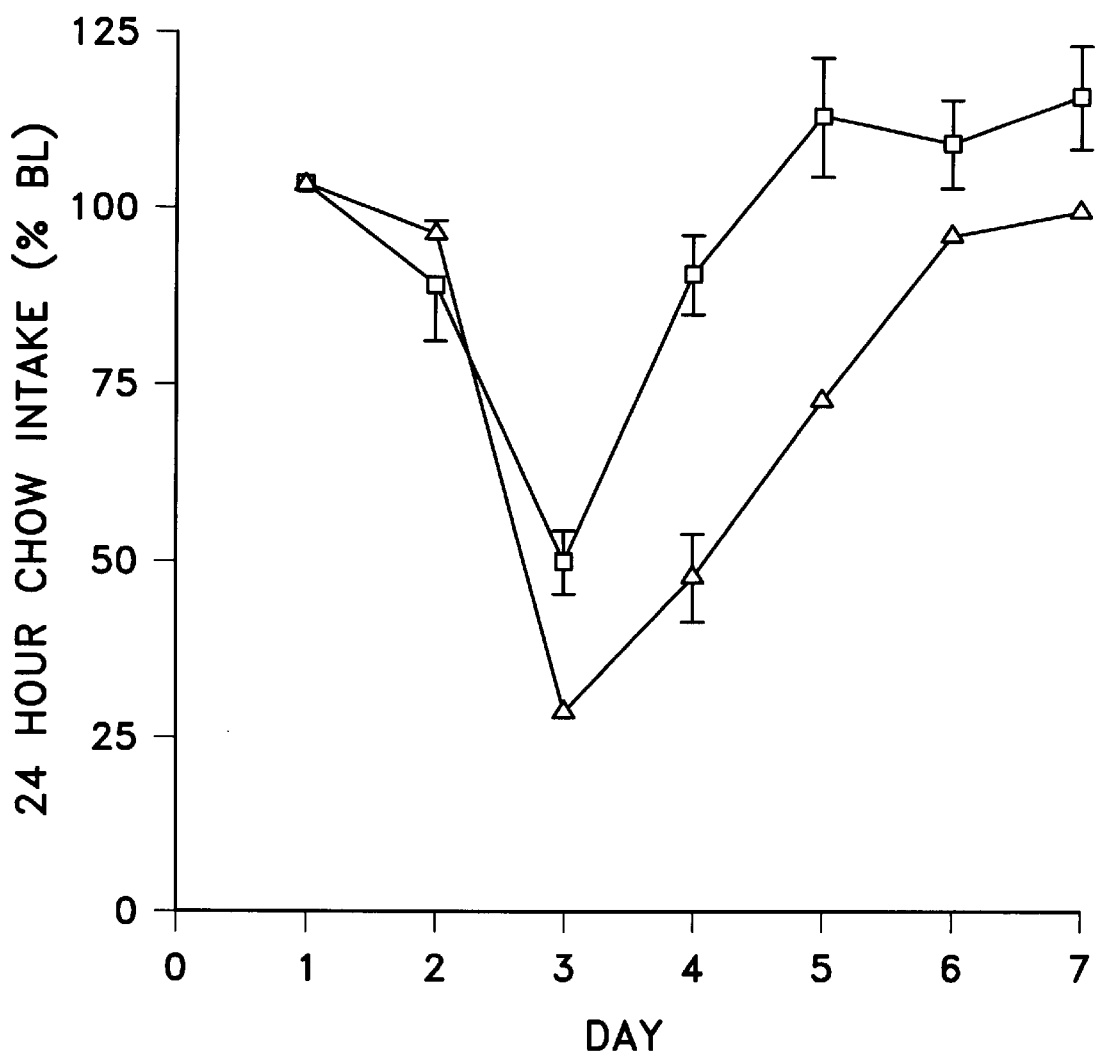
FIG. 4 illustrates prolonged feeding suppression in ob/ob mice (triangles), as compared to BALB/c mice (squares), following injection of fa/fa adipose conditioned medium.

The duration of feeding suppression in ob/ob and BALB/C recipients was also compared (FIG. 4). Briefly, 2 ob/ob or 3 BALB/c recipients received 2 intraperitoneal injections of fa/fa rat ACM (protein concentration=28.3±1.5 mg/ml) on day 2 of the assay. On day 1 and days 3–7 of the assay, the recipients received a daily intraperitoneal injection of PBS. Points represent the mean±SE expressed as a percent of baseline 24 h chow intake computed for the 3 days prior to test sample injection(s). The ob/ob recipients exhibited a protracted feeding suppression as compared to BALB/c recipients. For these reasons, ob/ob recipients were used in further experiments.

Example 6: Taste Aversion Test

A two bottle conditioned taste aversion test of fa/fa rat adipose conditioned medium was performed. Briefly, overnight fasted ob/ob test mice or control mice (n=5 per group) were trained over a 4 d period to drink flavor 1 liquid diet (vanilla Ensure™, Abbott Labs) for 2 h following a 1 ml intraperitoneal injection of phosphate-buffered saline (PBS; pH 7.4). On day 5, test mice were injected intraperitoneally with 1 ml of adipose conditioned medium (protein concentration=20 mg/ml) and control mice were injected intraperitoneally with 1 ml PBS. Both groups were then offered flavor 2 diet (chocolate Ensure™). On day 6, all mice were injected with 1 ml PBS, and both flavor 1 and flavor 2 were presented. As a positive control, test mice received 1 ml of 0.15M LiCl in water, control mice received 1 ml PBS, and both groups were offered flavor 3 diet (eggnog Ensure™) on day 7. On day 8, all mice were injected with 1 ml PBS, and both flavor 1 and flavor 3 were presented. The results are shown in Table 2.

TABLE 2

| | Volume Consumed (ml ± SD) | | | |
|---|---|---|---|---|
| | Flavor 1 | Flavor 2 | Flavor 3 | Total |
| Day 6 | | | | |
| Test | 5.9 ± 1.8 | 2.1 ± 1.8 | | 8.0 ± 0.36 |
| Control | 4.1 ± 2.3 | 3.8 ± 2.5 | | 7.9 ± 0.46 |
| p* | NS | NS | | NS |
| Day 8 | | | | |
| Test | 7.6 ± 0.81 | | 0.22 ± 0.13 | 7.8 ± 0.86 |
| Control | 5.1 ± 2.3 | | 2.4 ± 1.8 | 7.5 ± 0.64 |
| p* | 0.05 | | 0.03 | NS |

*Unpaired 2-tail t test with significance level of 0.05
NS: not significant

Taste aversion was not produced in test ob/ob mice by pairing injections of adipose conditioned medium with the presentation of a novel flavor (see Table 2, Day 6 results). In contrast, these same test ob/ob mice exhibited a taste aversion when lithium chloride, a nauseant, was paired with a novel flavor (see Day 8 results).

When this experiment was repeated, there again was no significant (p>0.05) taste aversion in test mice by pairing injections of ACM Keith the presentation of novel flavor 2. When these same test mice were examined for taste aversion by pairing injections of lithium chloride to flavor 3, a statistical difference (p=0.001) between flavor 1 and flavor 3 consumption was observed.

Example 7: Effect of Various Rodent Adipose Conditioned Media on Feeding Response in ob/ob Recipients To test the hypothesis that the ob/ob mutation results in partial or complete loss of ASF activity, ob/ob fat conditioned medium and other donor rodent fat conditioned media were examined for their effect on feeding after injection into ob/ob recipients. Briefly, conditioned media were prepared as described in Example 2, above. These media were concentrated to the protein concentration indicated in Table 3, below, and were then administered to ob/ob recipients by intraperitoneal injections of 1 ml aliquots. Response is expressed as percent of baseline 24 h chow intake in n separate assays. Analysis of variance indicated significant intergroup variability (F=34.174, p<0.0001).

TABLE 3

| Donor strain | n | Protein (mg/ml) | Response (%)* | p |
|---|---|---|---|---|
| ob/ob mouse | 8 | 21.2 | 91.1 ± 1.8 | — |
| db/db mouse | 4 | 21.0 | 72.3 ± 3.0 | 0.002 |
| Sprague Dawley rat | 2 | 16.6 | 73.3 ± 3.0 | 0.002 |
| fa/fa rat | 7 | 21.2 | 52.4 ± 3.0 | <0.0001 |

*mean ± SE

Table 3 shows that ob/ob donor adipose tissue conditioned medium did not result in a statistically significant suppression of the feeding response in ob/ob recipient mice. In contrast, the other rodent donor adipose tissue conditioned media did contain significant appetite down-regulating activity. In this experiment, the db/db donor mice were atypically small and young, and did not yield typical amounts of adipose tissue. Therefore, these particular db/db mice were not true matches for the other donor rodents tested. This fact may explain why the db/db ACM yielded responses that resembled those of normal rats, rather than fa/fa rats.

Figure 5:
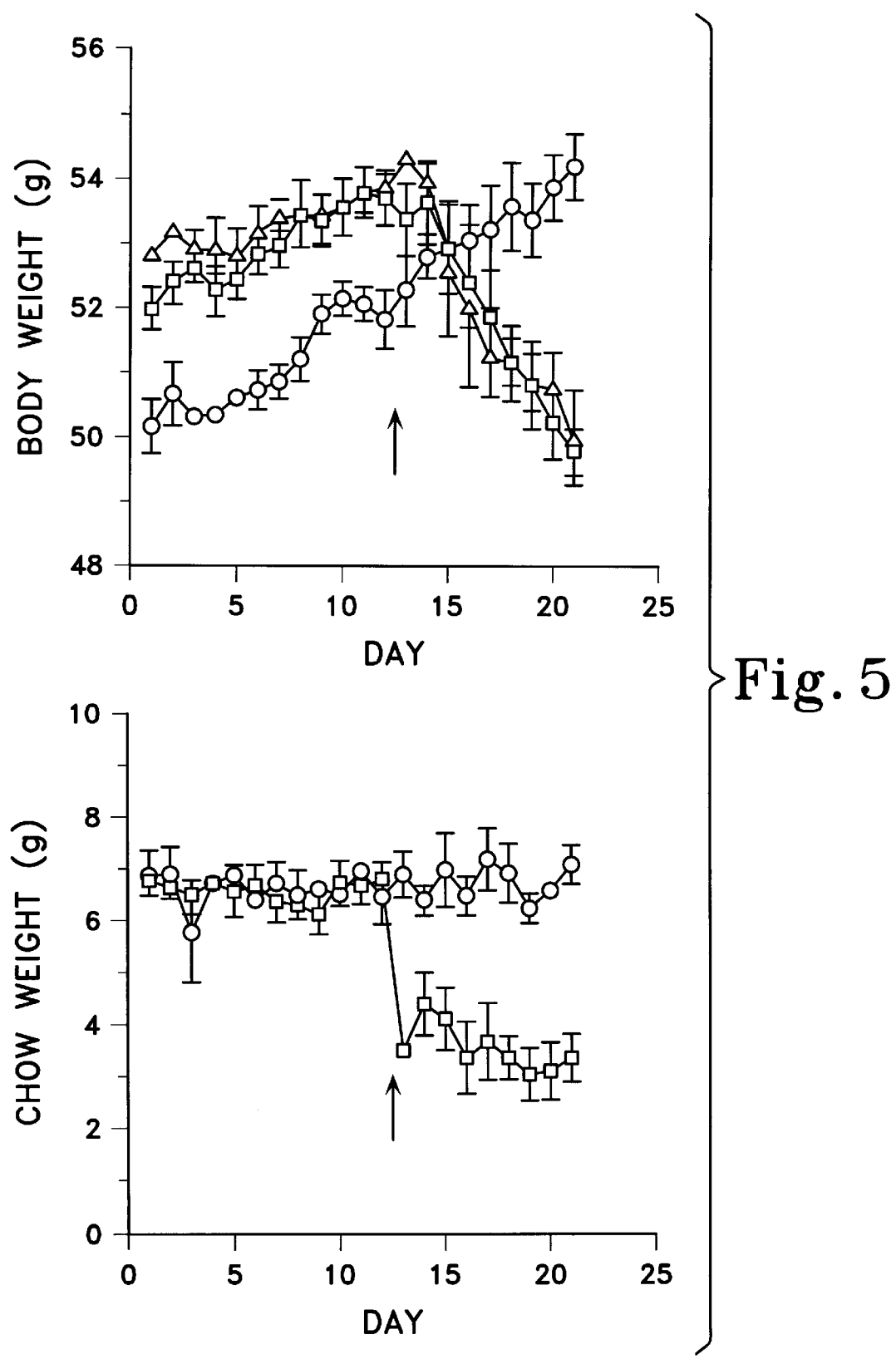
FIG. 5 depicts body weight and chow intake of ob/ob recipients that were injected with PBS for 12 d, then daily with fa/fa adipose conditioned medium (squares); with PBS throughout, and provided unlimited food (circles); or with PBS throughout, but after day 12 provided with an amount of chow that matched consumption by the test group that was injected with adipose conditioned medium.

Example 8. Determination of Weight Loss Associated with Injection of Adipose Conditioned Medium The effect of daily administration of adipose conditioned medium on body weight and chow intake of ob/ob recipients was determined. Briefly, four control mice (circles; see FIG. 5) each received a daily 1 ml intraperitoneal injection of PBS throughout the 21 day study period. Three test mice (squares) received 1 ml injections of PBS through day 12, then the daily injections were switched to 1 ml of fa/fa adipose conditioned medium (protein concentration=20 mg/ml). Three mice (triangles) received PBS injections throughout the study, but were fed chow weights identical to the amount of chow consumed by test mice on the previous day, beginning on day 12. All points represent the mean±SE.

A single daily injection of fa/fa ACM produced a sustained reduction in chow intake and progressive weight loss in ob/ob recipient mice, as compared to chow intake and weight loss in recipient mice that received a single daily injection of PBS (FIG. 5). ob/ob mice that were injected with PBS, but fed the same amount of chow as that consumed by ob/ob recipients that were injected with ACM, lost weight at an identical rate. These data demonstrate that reduced caloric uptake accounted for the weight loss in recipients that were injected with ACM yet had continuous access to chow. Further, these results are inconsistent with weight loss attributable to increased energy expenditure by the recipients as a result of injection with ACM.

When the ACM recipient group was switched to injection of PBS at day 25, the three recipient groups demontrated comparable body weights and chow intakes by day 45–50 and day 28, respectively. This comparability continued through the 60 day time course of the study.

Example 9. Partial Purification of ACM

Adipose tissue was excised from 10 fa/fa (Zucker) rats and ACM was prepared as in Example 2.A., above. Groups of 5, 3 and 2 rats served as donors on different days. The ACM generated from these three groups of rat adipose tissue each contained about 20 mg protein/ml after concentration. The discrete concentrated ACMs were stored on ice until pooling. Upon concentration, a 1 ml aliquot of each concentrated preparation was intraperitoneally injected into ob/ob recipient mice, resulting in a feeding response of 100%, 100% and 82% of baseline, respectively).

Briefly, 2220 ml of total ACM (conditioned using a total of 867.4 g adipose tissue) were concentrated by ultrafiltration, using a stirred cell apparatus and a 1 kD cut-off membrane (Amicon), to a a final, pooled volume of 100 ml. The concentrated preparation (100 ml) was dialyzed against 20 mM Tris buffer, pH 8.0, then passed through a 0.2 $\mu$m filter (Gelman; Ann Arbor, Mich.). This material was then applied to a 20 ml Q-Sepharose® ion exchange fast flow column (Pharmacia; Piscataway, N.J.; cross-linked agarose matrix that binds through quarternary amino groups that remain equally charged throughout the pH range 2–12) that had been equilibrated overnight with 20 mM Tris buffer (pH 8.0; 0.2$\mu$ filtered) at a flow rate of 0.1 ml/min. The concentrated preparation (125 ml) was loaded onto the column at 2 ml/min, washed with 20 mM Tris buffer, and the effluent was collected for about 65 min. The column was then washed for 20 minutes and the fractions independently collected. The column was then eluted using a 40 minutes 0–0.5M NaCl gradient. Fractions were monitored at $A_{220}$; collected (5 minutes; 10 ml); pooled (2 fractions per pool; i.e., 1+2=pool 1 and the like) through fraction 12; dialyzed and concentrated using an Amicon CentriPrep™ apparatus and a 3 kD cut-off membrane. Fractions containing wash effluent were concentrated using a stirred cell apparatus and a 1 kD cut-off membrane. Aliquots of the concentrated pools and column effluent were tested for appetite regulating activity. Column effluent means the material that flowed through the column upon application of the concentrated preparation.

TABLE 4

| Pool # | % Baseline |
|---|---|
| 1 | 103 |
| 2 | 70 |
| 3 | 90 |
| 4 | 75 |
| 5 | 90 |
| 6 | 97 |
| Effluent | 97 |

A 1 ml aliquot of each pool was injected into one recipient.
Each pool volume was about 6 ml.

Pool 2, which contained fractions 3 and 4, exhibited appetite suppression activity when tested in the assay described in Examples 1 and 3, above. These fractions eluted at a salt concentration of about 0.1–0.25M NaCl. Therefore, at pH 8.0, the active molecule(s) are slightly negatively charged, or exhibit a negatively charged region. Pool 4 (fractions 7 and 8; about 0.38–0.5M NaCl) demonstrated appetite suppression activity, but was less active than pool 2. Polyacrylamide gel electrophoresis analysis of pools 2 and 4 showed multiple protein bands, However, several protein bands in the concentrated preparation were eliminated or reduced in the pool 2 and 4 profiles, and several bands were enriched in the pool 2 and 4 profiles, as compared to the concentrated starting preparation.

Pools 2–5 above were assayed for protein content, with the following results: pool 2=21.4 mg/ml; pool 3=41.9 mg/ml; pool 4=31.9 mg/ml; and pool 5=10.2 mg/ml. These original pools 2–5 (6 ml each) were further concentrated with a CentriPrep™ apparatus to a volume of 2–3 ml/pool. These reconcentrated pools were bioassayed as above, with the following results: pool 2=63% of baseline chow intake (BL); pool 3=66% BL; pool 4=72% BL; and pool 5=75% BL. Therefore, ASF activity was present in pools 2–5 upon further concentration of the pools.

Subsequently, another large scale batch of ACM was prepared and partially purified as above. Three recipient animals per pool were tested in the bioassay, with the following results: pool 2=73% BL (8 mg/ml protein); pool 3=68% BL (23 mg/m protein); pool 4=93% BL (14 mg/ml protein); pool 5=95% BL (not determined). These data suggest that pool 2 material contained the greatest ASF activity on a mg protein basis.

Example 10. Prokaryotic Expression of a Representative ASF

A. Cloning and Expression of MBP:ob Fusion Protein in *E. coli*

(1) mouse ob

A representative appetite suppression factor (ASF) was expressed in *E. coli* as a maltose binding protein (MBP) fusion using an expression and purification kit obtained from New England BioLabs (Beverly, Mass.), according to the protocols supplied with the kit. Briefly, a mouse ob cDNA (SEQ ID NO:1) was prepared with Eco RI and Sal I adhesive ends and was cloned into the pMAL-c2 vector (New England Biolabs). The vector, pMALc2, was linearized with restriction enzymes Eco RI and Sal I, and treated with calf alkaline phosphatase. The vector and cDNA segments were gel purified. A ligation reaction containing 100 ng of purified vector and approximately 100 ng of cDNA was prepared and the resulting construct (MBP::ob fusion) was introduced into *E. coli* MC-1061 host cells (Clontech, Palo Alto, Calif.). LB plates containing 100 $\mu$g/ml ampicillin were inoculated with transformed cells. Colonies were isolated and plasmid DNA was prepared. Restriction analysis of the plasmid DNA identified colonies containing the in-frame fusion of the ob cDNA with the maltose binding protein cDNA. The constructs were further verified by sequence analysis. The verified clone, encoding ob protein with a Gln residue at position 49 (+Gln; SEQ ID NO:2), was designated pCZR90. An additional construct of mouse ob cDNA containing a nucleotide sequence (SEQ ID NO:5) that encodes ob protein without a Gln residue at position 49 (–Gln; SEQ ID NO:6) was constructed as described and designated pCZR100.

The MPB::ob fusion plasmids were expressed by cells cultured in rich medium (LB broth) containing ampicillin (250 $\mu$g/ml) to a cell density of ≈$10^7$ cells/ml ($OD_{600}$=0.1). After 1 h of growth at 37° C., expression of the MBP::ob fusion protein was induced by addition of isopropylthiogalactoside (IPTG) to a final concentration of 1 mM. Cultures were then incubated for an additional 3 h. Cells were recovered, disrupted by freezing and sonication, and the MBP-ob gene product fusion protein was recovered from a crude cell extract by affinity chromatography on amylose resin. The fusion protein was cleaved with factor Xa to liberate the ob gene product.

More specifically, protein extracts were prepared from IPTG-induced and control, uninduced cultures containing the pCZR90, pCZR100 and pCZR101 constructs, then analyzed by SDS-PAGE and Western blotting (see Example 11). Cells were harvested from 1.5 ml of culture, disrupted in 200 $\mu$l of lysis buffer (100 mM Tris, pH 7.0, 5% (w/v) SDS, 8M urea, 10% (v/v) glycerol, 2 mM EDTA, 0.01% bromophenol blue, 5% (v/v) β-mercaptoethanol) and ≈200 $\mu$l glass beads (Sigma; unwashed, 425–600 $\mu$m size) by vigorous vortexing and then heating to 65° C. Cell extracts were clarified by centrifugation and 5 $\mu$l samples were analyzed by SDS-PAGE. Coomassie blue staining of these gels revealed a predominant 60 kD band in induced samples that was not present in uninduced samples. Western blotting using anti-MBP antiserum (New England BioLabs) detected the induced band, demonstrating that the desired MBP::ob fusion protein was present in all three constructs.

One liter of *E. coli* culture harboring the murine MBP::ob construct, pCZR90 (+Gln), was prepared in "Fantastic medium" (Difco; 47.6 g powder and 4 ml glycerol per L $H_2O$). Expression and purification were performed as suggested by New England BioLabs (protocol # 800). SDS-PAGE analysis of the purified MBP::ob fusion protein indicated that ≧90% of total protein present was the fusion protein. Subsequently, pCZR101 and pMALc2 (vector with no cDNA insert) were similarly expressed and purified.

Uncleaved mouse MBP::ob fusion protein (+Gln) was injected into mice, as described in Examples 1 and 3. MBP protein was purified using the manufacturer's specfication, and was injected as a negative control. Approximately 65 $\mu$g of MBP protein and 50 $\mu$g of MBP::ob protein were used for the injections. The MBP-treated mice demonstrated appetite suppression of 91.5% of baseline, and MBP::ob-treated mice demonstrated appetite suppression of 63% of baseline.

(2) human ob

The human ob cDNA was isolated by screening a human fat cell 5' STRETCH PLUS cDNA library (Clontech, Palo Alto, Calif.) in lambda gt11. The library was plated according the manufacturer's specifications. A probe was generated by PCR using primers from the mouse ob sequence (SEQ ID NO:1). The library was screened as described and a positive clone was identified and designated #25. The human ob sequence (SEQ ID NO:3) was confirmed by sequence analysis.

DNA encoding the human ob cDNA was excised by digestion of the lambda gt11 clone #25 with restriction enzymes and ligated into the expression vector Zem229R (deposited with American Type Culture Collection, 12301 Parklawn Drive, Rockville, Md. as an *E. coli* HB101 transformant and assigned accession number 69447). The human cDNA in Zem229R was designated phOB-25 and included 5' and 3' untranslated regions and the coding region of the human ob sequence (SEQ ID NO:3). A construct containing human ob cDNA (SEQ ID NO: 3) prepared as described in 10.A. and designated pCZR101.

B. Generation and Purification of Anti-ob Antibodies

Rabbits were immunized (R and R Rabbits, Stanwood, Wash.) by initial subcutaneous injection of 250 $\mu$g purified MBP::ob fusion (murine or human ob) protein in Complete Freund's Adjuvant, followed by booster subcutaneous injections every three weeks thereafter with 125 $\mu$g purified MBP::ob fusion protein in Incomplete Freund's Adjuvant. After administration of the second booster injection, rabbits were bled 10 days after each boost and the serum was collected. For murine MBP::ob fusion protein injections, some rabbits received "native" fusion protein (untreated), and others received "denatured" fusion protein (heated to 65° C. in 1% (w/v) SDS in maltose-containing elution buffer (see Example 13) for 30 min).

To prepare monoclonal antibodies, mice were immunized with native MBP::human ob fusion protein (prepared in the same manner as the immunogen for rabbit polyclonal antibody production). The mice received a 50 $\mu$g primary injection, and 25 $\mu$g booster injections every two weeks, for at least 4 weeks. Hybridomas are prepared and clones screened and scaled up according to standard procedures (see, for example, Hurrell (ed.), *Monoclonal Hybridoma Antibodies: Techniques and Applications*, CRC Press Inc., Boca Raton, Fla., 1982).

Anti-ob antibodies were prepared by the following method. Anti-MBP antibodies were depleted using immobilized MBP columns. More specifically, two columns, each containing 20 mg of purified MBP linked to 10 ml of CNBr-SEPHAROSE 4B (Pharmacia, Piscataway, N.J.) were prepared using "native" MBP (untreated). Similarly, two additional columns were prepared using "denatured" MBP (heated to 65° C. in 1% (w/v) SDS in maltose-containing elution buffer (see Example 13) for 30 min) linked to CNBr-SEPHAROSE 4B. Rabbit antiserum raised against the native fusion protein was cycled through the two native MBP columns; rabbit antiserum raised against the denatured fusion protein was cycled through the two denatured MBP columns. Western blot analysis indicated that anti-MBP antibodies (present in either the native fusion protein antiserum or the denatured fusion protein antiserum) were essentially depleted. Each antiserum preparation retained the ability to recognize ob protein, as demonstrated by Western blotting.

Anti-ob-specific antibodies were obtained through affinity purification, using a 4 ml column containing 10 mg of either native MBP::ob fusion protein or denatured MBP::ob fusion protein linked to CNBr-SEPHAROSE 4B. The native protein column was used for the native protein antiserum; the denatured protein column was used for the denatured protein antiserum. Western blot analysis of these affinity purified anti-ob-specific antibodies showed that each antibody preparation specifically recognized ob protein, but not MBP. Also, all anti-ob reactivity was retained on the affinity column, and could not be detected in the column flow-through.

Example 11. Mammalian Cell Expression of a Representative ASF

A. mouse ob

A representative ASF was expressed in the BHK 570 (ATCC CRL 10314) cell line. Mouse ASF (ob) cDNA (SEQ ID NO:1) was inserted in the pDX expression vector (disclosed in U.S. Pat. No. 4,959,318) modified by inserting a new Sal I site at base pair 1395, as an EcoRI-SalI fragment. The resulting construct, designated pDX-mOB, was co-transfected into the host cells with Zem229R (deposited with American Type Culture Collection, 12301 Parklawn Drive, Rockville, Md. as an *E. coli* HB101 transformant and assigned accession number 69447) by the calcium phosphate method (Sambrook et al. *Molecular Cloning: A Laboratory Manual*, 2nd ed., Cold Spring Harbor Laboratory Press, Cold Spring Harbor, N.Y., 1989) using 16 µg pDX-mOB:5 µg Zem229R per 80% confluent 100 mm plate of cells. Transfected cells were grown in selection medium (growth medium plus 500 nm methotrexate; see Table 5) at 37° C. and 5% $CO_2$.

TABLE 5

Growth Medium 500 ml Dulbecco's Modified Eagle's Medium (DMEM) (Gibco, Gaithersburg, MD)
5% fetal calf serum (Hyclone, Logan, UT)
1 mM sodium pyruvate (Irvine, Santa Ana, CA)
0.29 mg/ml L-glutamine (JRH Biosciences, Lenexa, KS)
1× PSN (5 mg/ml penicillin, 5 mg/ml streptomycin, 10 mg/ml neomycin) (Gibco)

Confluent transfected cells were split into 150 mm culture dishes or 100 mm culture dishes in the selection medium described above and grown to confluency. Fresh medium was added by removing spent medium, rinsing the dishes in serum-free medium (see Table 6), and adding fresh serum-free medium to the culture dishes. The medium was conditioned for two days and then removed for further characterization.

TABLE 6

Serum-free Medium 250 ml of Ham's F12 medium (GIBCO-BRL, Gaithersburg, MD)
250 ml of Dulbecco's Modified Eagle's Medium (GIBCO-BRL)
0.01 mg/ml of transferrin (JRH Biosciences)
5 µg/ml of insulin (JRH Biosciences)
0.01 mg/ml of fetuin (Sigma, St. Louis, MO)
2 ng/ml of selenuim (Alrich, Milwaukee, WI)
1 mM sodium pyruvate (Irvine)
0.29 mg/ml L-glutamine (JRH Biosciences)

Cells were utilized for larger scale production of conditioned medium by removing cells from approximately five 150 mm culture dishes, resuspending in 1.5 liters of growth medium, seeding in cell factories (Nunc, Kamstrup, Denmark), and allowing the cells to grow to confluency. When cells were confluent, the growth medium was removed and serum-free medium was added.

When single culture dishes were used, serum-free medium did not contain insulin. Serum-free medium used for cell factories contained insulin.

The ability of conditioned medium to suppress appetite in test animals was assayed. Two-hundred and fifty milliters of conditioned serum-free culture medium was recovered from 150 mm culture dishes, filtered to removed cell debris, and concentrated 20-fold by ultrafiltration through an Amicon YM-1 76 mm membrane. The concentrated medium was assayed for appetite suppression activity as disclosed in Examples 1 and 3, above, using conditioned medium from cells transfected with Zem229R alone as a control (test samples, n=9; control samples, n=8). Feeding was reduced to 74±8.7% (mean±standard deviation) of baseline in the test animals, compared to 95±12% of baseline in controls.

Mouse ob-transfected cells secrete ob protein that is immunoreactive with anti-ob antibody, as demonstrated by three methods (1–3). The ob protein is also detectable by silver staining alone (4).

B. human ob

Human ASF (ob) cDNA (SEQ ID NO: 3) was isolated without the 5' and 3' untranslated regions (from nucleotide 108 to to nucleotide 549 of SEQ ID NO:3) and was inserted in the pZem229R expression vector utilizing Eco RI sites. The resulting construct, designated pCBhOB27, was transfected into Chinese hamster ovary DG44 cells (Urlaub et al., *Cell* 33: 405–412, 1983) using LipofectAMINE™ (GIBCO-BRL, Gaithersburg, Md.), according to the manufacturer's specification. Ten micrograms of plasmid DNA was used per 50–70% confluent 100 mm plate of cells. Transfected cells were grown in selection medium of α-MEM without nucleosides (JRH Sciences, Lenexa, Kans.) plus 250 nm methotrexate at 37° C. and 5% $CO_2$.

Confluent transfected cells are split into 150 mm culture dishes or 100 mm culture dishes in the selection medium described above and grown to confluency. Fresh medium is added by removing spent medium, rinsing the dishes in CHO-S-SFM II (GIBCO-BRL) serum-free medium, and adding fresh serum-free medium to the culture dishes. The medium is conditioned for two days and then removed for further characterization, as described below.

C. ob Protein Analyses (1) Radioimmunoprecipitation

First, $^{35}$S-labeled mouse ob protein was detected by radioimmunoprecipitation (RIP) of transfected cell conditioned medium. Briefly, cells transfected with either ob or control vector were seeded into 6-well culture plates and grown to confluency. The culture medium was aspirated, and DMEM, depleted of cysteine and methionine, and containing 1% fetal calf serum (FCS; 1 ml) and $^{35}$S EXPRESS (100 μCi/ml), was added to each well. The cells were incubated with the labeled medium for 6 h at 37° C. with 5% $CO_2$. After the incubation period, the medium was collected and the cells were discarded. Four hundred microliters of radiolabeled medium was placed in a microfuge tube and precleared with 50 μl PANSORBIN (Calbiochem). Rabbit anti-denatured mouse ob antibody (2.5 μl; as described in Example 10.B., supra) was added, and the antigen-antibody mixture was incubated for 3 h on ice. After incubation, 40 μl of PANSORBIN was added, and the mixture was incubated for 15 min on ice. The mixture was removed from the ice, spun in a microfuge for 30 sec, and the resulting pellet was washed in Penman Lysis Buffer (10 mM HEPES, 50 mM NaCl, 2.5mM $MgCl_2$, 0.3M sucrose and 1% Triton X-100, pH 7.4) or RIPA buffer (10 mM Tris, pH 7.4, 1% sodium deoxycholate, 1% Triton X-100, 0.1% SDS, 5 mM EDTA and 0.15M NaCl). The resultant pellet was then resuspended in 20 μl of standard SDS-PAGE sample loading buffer. For some experiments, the resultant pellets were resuspended in SDS-PAGE sample loading buffer under reducing or non-reducing conditions (±β-mercaptoethanol). The SDS-PAGE samples were electrophoresed using preformed 10–20% miniplusTC SEPRAGELS (Integrated Separation Systems, Natick, Mass.).

When radiolabeled protein was precipitated with affinity purified anti-ob antibodies raised against denatured MBP::ob fusion protein and resultant SDS-PAGE samples were prepared under reducing conditions, no bands were detected in the control vector sample, but a prominent band was seen (≈14–16 kD) in the ob transfected sample.

When radiolabeled protein was precipitated with affinity purified anti-ob antibodies raised against native MBP::ob fusion protein and SDS-PAGE samples were prepared under non-reducing conditions, a prominent band of ≈14 kD was detected in the ob-transfected sample that was absent in the control vector sample. When radiolabeled protein was precipitated with affinity purified anti-ob antibodies raised against denatured MBP::ob fusion protein and SDS-PAGE samples were prepared under non-reducing conditions, no prominent bands were detected in the control vector sample, but prominent bands were seen at ≈14–16 kD and at ≈30 kD in the ob transfected sample. These bands may represent monomer and dimer forms of ob protein expressed in BHK cells.

(2) Western Blotting

Second, mouse ob protein, was detected by Western blotting of concentrated or unconcentrated ob transfected cell conditioned medium. Briefly, ob transfected or control vector cells were grown, as described in (1) above. Aliquots of conditioned medium (untreated or concentrated by ultrafiltration) were prepared in reducing or non-reducing SDS-PAGE sample preparation conditions, and electrophoresed as in (1) above. The gels were electroblotted onto nitrocellulose at 40V overnight (transfer buffer=56 g glycine and 12 g Tris base in 3.2 L $H_2O$ and 0.8 L methanol). The nitrocellulose was blocked for 1 h or overnight in Western A (blocking) buffer (50 mM Tris, pH 7.4, 5 mM EDTA, 0.05% NP-40, 150 mM NaCl and 0.25% (w/v) gelatin). Rabbit polyclonal antiserum raised against denatured MBP::ob fusion protein (i.e., primary antibody) was added at a 1:5,000 dilution in Western A buffer and incubated for 1 h. The dilute antiserum was removed, the nitrocellulose washed in Western A buffer, and goat anti-rabbit immunoglobulin (Ig) conjugated to horseradish peroxidase (i.e., secondary antibody) was added at a 1:10,000 dilution in Western A buffer. After 1 h, the dilute goat anti-rabbit Ig was removed, the nitrocellulose washed with Western A buffer, and ob protein bands were visualized using chemiluminescence (ECL luminescence kit; Amersham, according to the manufacturer's instructions) and exposure to X-ray film.

When SDS-PAGE samples were prepared under reducing conditions and blotted using antiserum raised against denatured MBP::ob fusion protein, no bands were detected in the control vector sample, but a prominent band was seen (≈14–16 kD) in the ob transfected sample.

When SDS-PAGE samples were prepared under non-reducing conditions and blotted using antiserum raised against denatured MBP::ob fusion protein, no prominent bands were detected in the control vector sample, but prominent bands were seen at ≈14–16 kD and at ≈30 kD in the ob transfected sample. These results are consistent with those obtained using RIP.

(3) Cold Immunoprecipitation (IP)

Third, unlabeled cells were prepared and processed by the same method as described for $^{35}$S-RIP samples in (1) above, except that 200 μl of unlabeled supernatant (concentrated ≈15X) was combined with rabbit antiserum raised against denatured MBP::ob fusion protein. These "cold IP" samples were subjected to SDS-PAGE, and then were Western blotted, as described in (2) above, or silver stained.

An SDS-PAGE sample of cold IP material that was Western blotted with anti-denatured MBP::ob fusion protein antibodies demonstrated ob protein at ≈14–16 kD in the ob transfected sample, which was absent in the control vector sample.

A sample of cold IP material that was precipitated with rabbit antiserum raised against denatured MBP::ob fusion protein; prepared using SDS-PAGE sample loading buffer containing β-mercaptoethanol (reduced); then electrophoresed and silver stained, exhibited a prominent band at ≈14–16 kD in the ob transfected sample, which was absent in the control vector sample. Similar ob and control samples that were precipitated with rabbit antiserum raised against denatured MBP::ob fusion protein; prepared using SDS-PAGE sample loading buffer without β-mercaptoethanol (unreduced); then electrophoresed and silver stained, showed a prominent band at ≈30 kD in the ob transfected sample, which was absent in the control vector sample.

(4) Silver Staining

When concentrated, ob-transfected conditioned medium and concentrated, control vector conditioned medium were prepared using SDS-PAGE sample loading buffer containing β-mercapt-ethanol (reduced), then electrophoresed and silver stained, a prominent band was visible at ≈14–16 kD in the ob transfected sample, which was absent in the control vector sample.

D. Analyses of Additional Metabolic Effects

The effect of chronic intraperitoneal administration of recombinant mouse ob protein on recipient serum insulin and glucose levels was determined. Briefly, orbital blood was collected from ob/ob mice before and immediately following 2 weeks of daily 80 μg injections of recombinant mouse ob protein (n=6) or of ZEM control medium (n=3). Insulin levels in the mice that received recombinant ob protein decreased from 122±11 ng/ml at day 0 to 10±1.9 ng/ml at day 14 (p=0.0002); glucose levels decreased from 489±44 mg/dl to 167±8.9 mg/dl (p=0.0007). Insulin levels in the mice that received the control ZEM medium preparation decreased from 427±114 ng/ml at day 0 to 275±68 ng/ml at day 14 (not statistically different); glucose levels increased from 427±81 mg/dl to 448±87 mg/dl (not statistically different). Thus, administration of recombinant ob protein provides a salutary effect on insulin sensitivity in recipient mice. These data may reflect a direct effect of exogenous ob protein on insulin sensitivity, or may represent an indirect effect of injected ob protein activity (since ob protein induced weight loss in recipients that were injected with ob protein).

Example 12. Mammalian Expression of His-Tagged ASF

A His-tagged mouse ob CDNA construct was expressed in BHK 570 cells. An inframe tract of six histidine codons was added to the 3' end of the ob coding sequence by PCR using the mouse PCR-generated CDNA as template. The resulting PCR product was inserted into the vector pHZ-200, a vector comprising the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-200 contains an E. coli origin of replication, a bacterial beta-lactamase gene, a mammalian selectable marker expression unit comprising the SV40 promoter and origin, a dihydrofolate reductase gene and the SV40 transcription terminator. The resulting plasmid was transfected into BHK 570 cells. Transfectants were selected in 1 lM methotrexate. The tagged ob protein was isolated from conditioned culture medium by passing the medium over a column of metal chelation resin containing immobilized Ni2+ (HIS-BIND™, Novagen, Madison, Wis.). Bound protein was eluted from the column with 500 mM imidazole.

An inframe tract of six histidine codons and a 4 amino acid spacer (Gly Gly Ser Gly) were added to the 5' end of the mature ob coding sequence by PCR using the mouse cDNA described above. The resulting PCR product was inserted into the vector pHZ-200 along with a 100 base pair fragment containing the tPA signal sequence for efficient secretion of the ob protein. The resulting plasmid was transfected into BHK 570 cells, and the 5' tagged protein was isolated as described above. Western blot analysis of the N-terminal His-tagged protein showed that the major product was a doublet of bands at approximately 18 kD, with the C-terminal His-tagged protein appeared as a doublet at about 16 kD.

Figure 6:
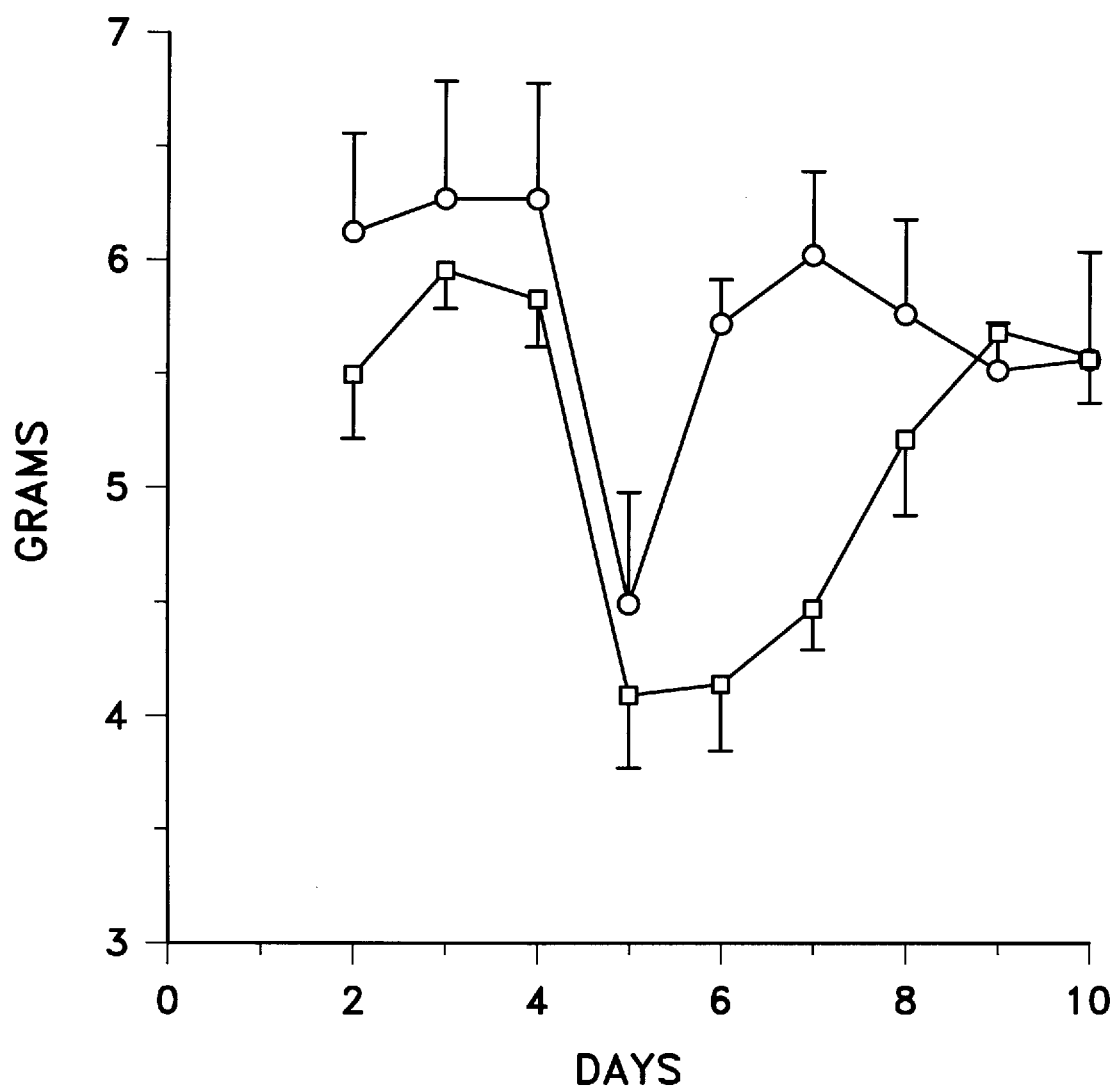
FIG. 6 illustrates that when a single injection of N-terminal Histidine tagged ob protein is administered to ob/ob mice, the effect of appetite suppression is prolonged compared to the effect of unmodified ob expressed in BHK cells.

The N-terminal and C-terminal tagged ob proteins were assayed for activity in mice (as described in Examples 1 and 3). C-terminal tagged ob protein did not demonstrate significant appetite suppression, while N-terminal protein suppressed appetite to 70% of baseline, suggesting that modification of the C-terminus inactivated the ob protein. The effect of the single injection of 25 μg of N-terminal tagged protein, as shown in FIG. 6, was prolonged suppression of appetite when compared to unmodified ob produced by BHK cells.

Example 13. Purification of ob Protein

A. Purification From MBP::ob Fusion Protein Expressed in Prokaryotic Cells
(1) Amylose Column Chromatography of MBP::ob Protein MBP::ob fusion protein was induced in transformed E. coli with IPTG, as described in Example 10 above, and purified by amylose column affinity chromatography.

Briefly, induced cells were collected and the weight of the cell pellet was determined. The cell pellet was resuspended in lysis buffer (column buffer (20 mM Tris, pH 7.4 containing 200 mM NaCl) containing 5 mM EDTA, 10 mM β-mercaptoethanol and 2 mM PMSF), adding 10 ml lysis buffer per gram of cell pellet. The cell suspension was placed on ice and sonicated for a 1 min period in five separate bursts, with a 5 min wait between each sonication burst. If the volume of the cell suspension was greater than 50 ml, the sonication was done in six to seven 1 min bursts, or in five 2 min bursts. The sonicated preparation was then centrifuged at 15,000 RPM for 30 min at 4° C. The supernatant was decanted, and the pellet discarded.

A 50 ml amylose resin column (2.5 cm×9.4 cm) was equilibrated in column buffer (20 mM Tris, pH 7.4 containing 200 mM NaCl) at 4° C. This volume of resin was calculated to be sufficient to bind at least 150 mg of fusion protein. The post-sonication supernatant was loaded onto the column at a rate of 1 ml/min. The loaded column was washed with 10 column volumes of column buffer, and then connected to a fraction collector. The column was eluted with elution buffer (column buffer containing 10 mM maltose) at 1 ml/min, and fractions were collected every 5 min. Typically, a peak started at about fraction 5 and continued for about 8–10 fractions. Elution was continued until the absorbance at 280 nm was baseline.

The peak fractions (>0.7 OD) were determined by monitoring at 280 nm and at 320 nm. The $A_{320}$ reading was subtracted from the $A_{280}$ reading, to compensate for light scattering. The peak fractions were pooled, and protein concentration was determined by $A_{280}$–$A_{320}$ absorption.

MBP, E=1.48 $Au(cm^{-1})((mg/ml)^{-1})$; MBP::ob, E=1.16 $Au(cm^{-1})((mg/ml)^{-1})$

MOB=0.157 calculated and 0.489 by amino acid analysis

The fusion protein was estimated to be about 85% pure after amylose column purification, as determined by SDS-PAGE densitometry.

The protein was concentrated to about 6 mg/ml using Amicon 10K CentriPreps, or applied to a hydroxyapatite column. The amylose column was regenerated by removing the column from the cold room and washing: (i) with 2–3 column volumes of deionized (DI) water; (ii) with 3 column volumes of 0.1% SDS; (iii) with 10 column volumes of DI water; and (iv) with 2 volumes of column buffer.

(2) Factor Xa Cleavage of the MBP::ob Fusion Protein

The MBP::ob fusion protein contains a Factor Xa proteolytic cleavage site near the site of fusion. Upon Factor Xa cleavage, the ob protein, with a 4 amino acid (Ile-Ser-Glu-Phe; ISEF) leader, was released.

Briefly, the fusion protein can be cleaved in elution buffer. However, if cleaved MBP was to be removed from the cleaved mixture by re-passage over an amylose column, free maltose (present in the elution buffer) was removed from the purified MBP::ob preparation prior to cleavage.

Bovine Factor Xa (1% (w/w)) was combined with purified MBP::ob fusion protein in 20 mM Tris, pH 7.0, containing 200 mM NaCl. This cleavage solution was incubated at 20° C. for 18 h with gentle agitation or rocking. The solution was then centrifuged for 15 min at 10,000 RPM at 4° C. to remove denatured protein.

The decanted supernatant was a mixture of: (i) correctly folded ob protein; (ii) incorrectly folded ob protein; (iii) multimeric species of ob protein; (iv) released MBP; and (v) about 9% uncleaved MBP::ob protein. About ⅓ of the ob protein was soluble; the remainder formed a precipitate. Most of the MBP was found in the soluble fraction, whereas the uncleaved MBP::ob protein was mainly found in the precipitate.

(3) Purification of ob Protein

The cleaved ob protein was purified by reverse phase chromatography using either a C4 or C8 column. Other reverse phase chromatography matrices may be suitable.

Specifically, the Factor Xa-cleaved ob protein was added to 10 mM Tris, pH 7.0, containing 5M freshly made urea and 100 mM β-mercaptoethanol, and incubated at 50° C. for 30 min. The reduced, unfolded protein was loaded onto a Vydac #214TP1022 C4 (2.2 cm×25 cm, 5μ, 300 Å) column at 10 ml/min. The column was previously equilibrated in 27% acetonitrile (Acn)/0.1% trifluoroacetic acid (TFA). A 60 min gradient was started from 27% Acn/1% TFA to 72% Acn/1% TFA at a flow rate of 10 ml/min. The chromatography was monitored at 215 nm, 2 OD full scale, and 0.5 min fractions were collected. The column volume was about 80 ml. MBP protein eluted at 37.8% Acn, followed by uncleaved MBP::ob fusion protein at 46.6% Acn and ob protein at 47.6% Acn. Amino acid sequencing data, amino acid analysis, and mass spectroscopy data all confirmed the predicted composition as ISEF-ob protein.

The precipitate and the soluble material that result after Factor Xa cleavage can be purified as a combined preparation or as separate (soluble and insoluble) fractions. Purification of ob protein from the precipitate yielded ob protein of higher purity, probably because the large MBP peak in the soluble fraction tailed into the desired ob peak.

Human ob protein and mouse ob protein (native, non-fusion form) expressed in BHK cells were purified using the same method. These proteins exhibited slightly different column retention times that were consistent with the absence of the ISEF leader sequence in these ob protein preparations.

(4) Refolding and Oxidation of ob Protein Thiols

Pooled ob protein, present in C4 reverse phase chromatography fractions (prepared in A.(3), above) was lyophilized to remove Acn/TFA. The lyophilized preparation was redissolved in argon-sparged 10 mM Tris, pH 7.0, containing 5M urea, and the ob preparation was then reduced using a 20× excess (M/M thiols) of EKATHIOL resin (Ekagen, Menlo Park, Calif.; resin that contains a thiol red/ox functional group that reduces peptide thiol groups). Standard reducing agents, such as dithiothreitol, β-mercaptoethanol, and glutathione, may be substituted for EKATHIOL resin.

After 1 h at room temperature, the resin was removed and a 20× excess of EKATHIOX resin (Ekagen; resin contains a thiol red/ox functional group that oxidizes peptide thiol groups) was added. The resin was removed and the supernatant was dialyzed against 200 volumes of argon-sparged 10 mM Tris, pH 7.0, for 18 h. About 50% of the ob protein was soluble after dialysis, with about 9–13% present in dimer or multimer form; the remainder was present in monomer form. SDS-PAGE showed that ob protein migrated faster in non-reduced form than in reduced form, indicating that it is intra-disulfide bonded. The resultant purified protein was active in the ob bioassay (recipients described in Example 1 received one intraperitoneal injection of 55 μg purified ob protein; mean % of baseline= 71±22; n=3).

The insoluble precipitate that results after Factor Xa cleavage of MBP::ob fusion protein was resubjected to this reduction/oxidation process, and provided about the same % yield of refolded protein.

(5) Separation of Monomer and Dimer/Multimer Forms

Monomeric ob protein was separated from dimer/multimer forms of ob protein by chromatography on a C4 column, as described in A.(4), above. The ob dimer eluted at 47.6% Acn; the ob monomoer eluted at 52.8% Acn. This repurified, monomeric protein, which contained about 2% ob dimer, was freely soluble in 10 mM Tris, pH 7.0, after lyophilization. This repurified, monomeric ob preparation displayed equivalent activity in the ob bioassay as the original, refolded material.

B. Purification of ob Protein Expressed in Mammalian Cells (1) Q-Fast Flow Sepharose Chromatography BHK cells expressing mouse ob protein (BHK/ob) produced conditioned medium that was sterile filtered and 10× concentrated. This concentrated material was buffer exchanged into 20 mM Tris, pH 8.0 buffer, and the resultant material had a conductivity of 1 milliSeimen. Optionally, the pH of this material was raised to pH 8.5 to improve binding to Q-Fast Flow Sepharose (Pharmacia). At this pH, the material transported through the column as a tight band during loading. The rate of transport through the column determined the sample volume that was loaded.

Upon completion of sample loading, elution was aided by initiating a gradient between (i) 20 mM Tris, pH 8.5 and (ii) 20 mM Tris, pH 8.5, containing 1M NaCl. Typically, for a 100 ml Q-Fast Flow Sepharose column, a flow rate of 10 ml/min was used, with the gradient developed from 0% to 30% 1M NaCl over 30 min. The ob protein eluted (with contamination) as a large, almost "square wave", peak. A slight degree of separation between monomer and dimer ob protein was observed, with the dimeric form eluting as slightly larger than the monomer form.

(2) MonoQ Chromatography: Monomer and Dimer Separation

Monomer and dimer forms of ob protein were resolved using FPLC (fast protein liquid chromatography) and MonoQ resins. The same buffer conditions as described for Q-Fast Flow Sepharose (B.(1), above) were employed, but lower flow rates and less steep gradients were beneficial. Typically, a flow rate of 1 ml/min and a gradient from 0% to 20% of 1M NaCl over 30 min separated the monomer and dimer species of ob protein.

(3) Phenyl Sepharose Chrometography

Alternatively, concentrated BHK/ob conditioned medium was chromatographed using phenyl Sepharose (Pharmacia), with an acceptable resultant purification. Briefly, concentrated BHK/ob conditioned medium was adjusted to pH 5.7 in 20 mM MES (morpholinoethanesulfonic acid) containing 1M NaCl. This material was chromatographed using a column of phenyl Sepharose that had been previously equilibrated in the same buffer (20 mM MES, pH 5.7, containing 1M NaCl). Some major contaminants "passed through" during sample loading, but ob protein was bound to the matrix. The column was then washed with starting buffer, and some additional contaminants were eluted, while ob protein remained bound. The bound ob protein was eluted with 20 mM Tris, pH 8.0. The material eluted was significantly purified over the starting material, particularly by removal of a very prominent contaminant.

(4) Hydroxyapatite Chromatography

In yet another alternative, concentrated BHK/ob conditioned medium was adjusted to pH 6.8 in 5 mM MES buffer. This material was passed over a column of hydroxyapatite that had been previously equilibrated in the same 5 mM MES, pH 6.8 buffer. Most of the proteins, including all of the ob protein, were bound to this matrix during sample loading. The column was then washed with starting buffer, prior to elution of ob protein. The ob protein eluted at a "step" to 10 mM potassium phosphate (KP) buffer, pH 6.8. Other major contaminants eluted at 50 mM KP to 300 mM KP. The ob protein obtained by this method was considerably purified compared to the starting material.

C. Direct Capture and Purification of ob Protein from Unconcentrated BHK Conditioned Medium Recombinant mouse ob protein was directly captured from 1× BHK/ob cell factory medium. Briefly, the BHK/ob conditioned medium was adjusted to 1M in NaCl, 20 mM in MES, and pH 5.7 (with 2N NaOH). The protease inhibitor phenylmethylsulfonyl-fluoride (PMSF) was added to a final concentration 0.6 mM. The adjusted medium was pumped through a 0.45 micron filter onto a bed of Fast Flow Phenyl Sepharose equilibrated in 1M NaCl, 20 mM MES, pH=5.7 (equilibration buffer). A 500 ml column with an 11.0 inch diameter was loaded at 60 ml/min. The ob protein sticks tightly to the column under these conditions. Upon completion of sample loading (up to 30 liters of 1× medium), the column was washed with 5 column volumes of equilibration buffer. Bound proteins were then eluted with 5 mM borate buffer at pH=8.5. During elution, the flow rate was reduced to 12 ml/min, and 18 ml fractions were collected. The ob protein eluted as a symmetric peak between fractions 40 and 60. The recovery of ob protein was greater than 95%, judged by analytical HPLC on a C4 reverse phase column.

The pooled material from the Phenyl Sepharose step had a conductivity of about 8 milliSeimens. This pooled material was adjusted to 20 mM MES, and the pH was titrated to 6.8. A 2×5 cm column packed with 80 micron ceramic hydroxyapatite was equilibrated in 0.1M NaCl, 20 mM MES, pH=6.8 buffer. The protein was passed through the column bed at 2 ml/min, and the effluent was collected. When the sample load was completed, the column was washed with equilibration buffer, with continued effluent collection, until the absorbance returned to baseline. Reverse phase (C4) HPLC demonstrated high recovery and substantial purification of ob protein. At this point, however, the material was only partially purified.

If ob protein retains biological activity at acid pH (≈pH 5.0), MonoS® (charged sulfonic groups that remain negative over a pH range of 2–12, attached to a pH-stable, beaded hydrophilic resin; Pharmacia) ion exchange is used for purification of ob protein. S-Sepharose® (sulfopropyl Sepharose; Pharmacia) tightly bound ob protein at pH=4.9, 10 mM acetate buffer. The bound proteins were eluted with an ionic strength gradient, and ob protein eluted at fairly high ionic strength (i.e., at 300–500 mosm in NaCl). These data suggest that ob protein is amenable to MonoS purification. Alternatively, following determination of low pH protein activity/stability, the bound proteins are eluted using an ascending pH gradient The ob protein is expected to start eluting at about pH=7.0.

D. Effect of Metal Ions

Some data suggest that metal ions complex with the ob protein. Briefly, ob protein from the Phenyl Sepharose pool material was dialyzed into borate-buffered saline (120 mM NaCl, 2.7 mM KCl, and 10 mM boric acid, pH=7.4), with and without "trace metals" added. The borate buffer with trace metals added contained the following: 10 $\mu$M $ZnCl_2$; 17 $\mu$M $CaCl_2.2\ H_2O$; 8 $\mu$M $Na_2MoO_4.2\ H_2O$; 5$\mu$M $CuSO_4$; and 100 $\mu$M $FeCl_3.6\ H_2O$. Under these conditions, some of the $FeCl_3$ trace metal component precipitated out of solution. The biological activity of the ob protein pool material that was dialyzed against borate-buffered saline plus trace metals was significantly higher than that of the same material dialyzed against non-metal-containing borate buffer. When borate-buffered saline plus trace metals (vehicle) was tested in the mouse bioassay, no suppression of chow intake was observed. The particular metal(s) and concentrations that enhance recombinant ob protein acitivity are determined using routine procedures known in the art.

Example 14. Yeast Expression of a Representative ASF

A. Cytoplasmic ob Construct

Figure 7:
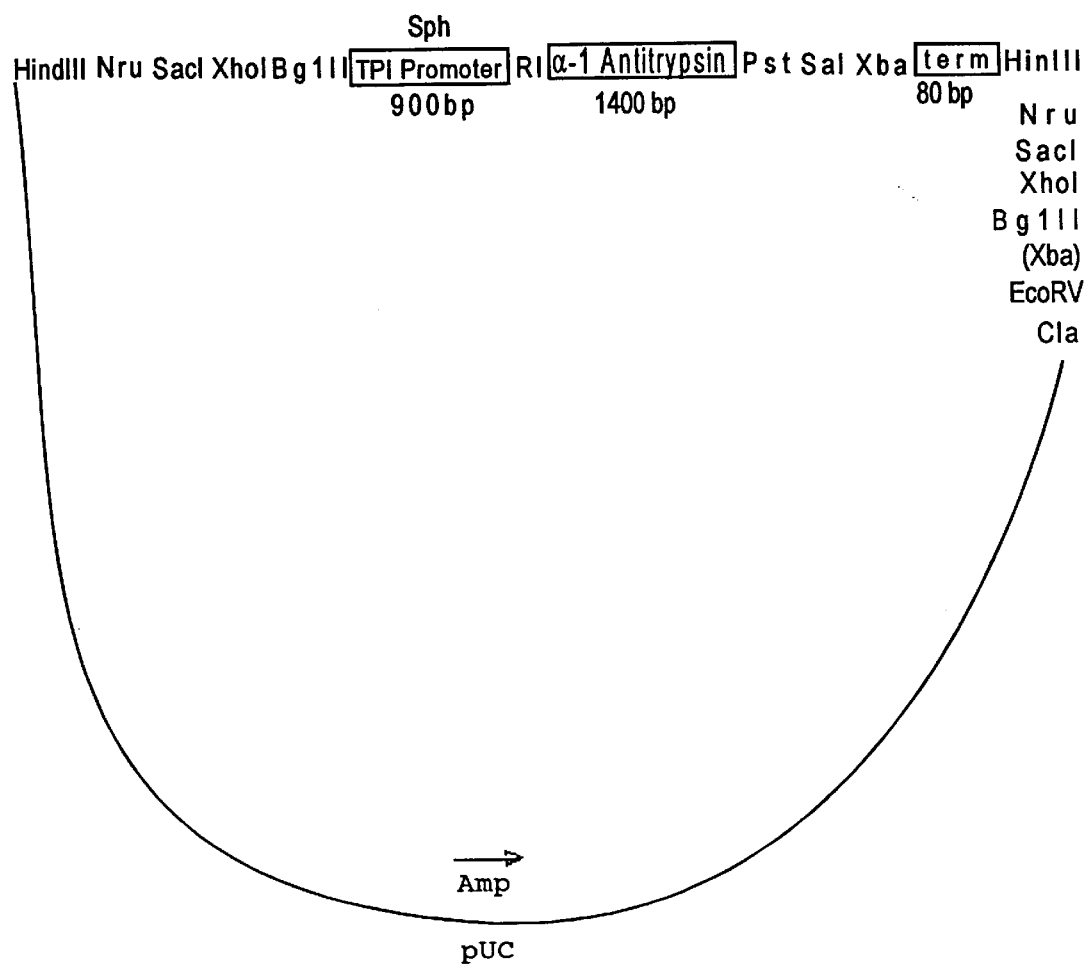
FIG. 7 shows the vector pMVR1.

The plasmid, designated pCZR108, was constructed to express a cytoplasmic form of the human ob protein. It consists of the ADH4$^c$ promoter, the coding region for the mature portion of the human ob protein (amino acid residue 22 to amino acid residue 167 of SEQ ID NO: 3), and the TPI terminator. The pUC-based plasmid pMVR1 (FIG. 7) was linearized with Sna BI and Sal I restriction enyzmes. The yeast ADH4$^c$ promoter (Ciriacy et al., *Molec. Gen. Genet.* 176:427–431, 1979) was isolated as a 1250 base pair Bam HI (blunted with T4-polymerase) to Eco RI fragment. A 450 base pair coding region of the mature form of the human ob protein (from nucleotide 108 to to nucleotide 549 of SEQ ID NO:3) was isolated as an Eco RI to Sal I fragment. The 90 base pair TPI terminator present in pMVR1 as a Sal I and Bgl II fragment. The pMVR1 vector was digested with Sna BI and Eco RI. The linearized vector was ligated with the ADH4$^c$ promoter fragment that had been blunted using T4 polymerase. The resulting plasmid was designated pCZR105 and contained the TPI terminator from pMVR1. The mature human ob coding region was amplified using PCR with primers ZC8769 (SEQ ID NO: 7) and ZC8699 (SEQ ID NO: 8) to introduce Eco RI and Sal I sites. The amplified DNA was gel purified and ligated into pCZR105 that had been linearized by digest with Eco RI and Sal I. The resulting cytoplasmic human ob protein expression cassette plasmid was designated pCZR107.

pCZR107 was subcloned as a Bgl II fragment (from pCZR107) into the Bam HI site of the POT vector pCZR12 to give pCZR108. pCZR12 is derived from pDPOT (deposited with the American Type Culture Collection as ATCC No. 68001); it carries a wild-type LEU2 gene instead of the LEU2-D allele in pDPOT.

B. Secreted ob Construct

Plasmids pCZR112 and pCZR113 were constructed to express secreted forms of the human ob protein. The plasmids were made as fusions to the yeast α-Factor prepro segment. In pCZR112, the region encoding the Lys-Arg residues at the end of the α-Factor prepro segment are joined directly to the region encoding the mature N-terminal residues of the human ob protein. In pCZR113, codons that encode a Glu-Ala dipeptide are inserted between the α-Factor prepro Lys-Arg and the N-terminal residues of the human ob protein.

The expression cassettes in plasmids pCZR112 and pCZR113 each contain: 1) a 900 base pair TPI promoter fragment from pMVR1; b) a 250 base pair α-Factor prepro region; c) a 450 base pair human ob protein coding region and 4) a 90 base pair TPI terminator fragment from pMVR1. Val-Pro-Ile-Gln-Lys begins at amino acid residue 22 of SEQ ID NO: 4 and is the amino acid sequence of the mature N-terminus of the human ob protein. Using a polymerase chain reaction and the oligonucleotide primers ZC8702 (SEQ ID NO: 9) and ZC8699 (SEQ ID NO: 8) a plasmid with the 5' sequence of Lys-Arg was generated and designated pCZR110. A second plasmid, designated pCZR111, was generated by polymerase chain react-on using the oligonucleotides ZC8701 (SEQ ID NO: 10) and ZC8699 (SEQ ID NO: 8), and has a 5' sequence of Lys-Arg-Glu-Ala. The oligonucleotide ZC8699 (SEQ ID NO: 8) introduces a Sal I site at the 3' end of the human ob sequence.

The two secreted forms of the human ob expression vectors were made by first subcloning the 250 bp Eco RI-Hind III alpha factor prepro segment and the 100 bp Hind III—Sal I coding region from the 3' end of the human ob cDNA into Eco RI and Sal I digested PMVR1$^{H-}$ in a three part ligation (pMVR1$^{H-}$ is a modified version of pMVR1 lacking Hind III sites). This intermediate plasmid was called pCZR104. The two secreted form of the human ob coding sequence were amplified by PCR with primers ZC8702 (SEQ ID NO: 9) and ZC8699 (SEQ ID NO: 8) or ZC8701 (SEQ ID NO: 10) and ZC8699 (SEQ ID NO: 8). pCZR104, was linearized with Hind III, and PCR fragments encoding the secreted forms of human ob that had been digested with Hind III were inserted into this site to generate the full length secreted human ob protein expression cassettes.

The expression cassettes from plasmids pCZR110 and pCZR111 were subcloned as Bgl II fragments into the Bam HI site of pCZR12 to give pCZR112 and pCZR113, respectively.

C. Expression of Yeast ob

Plasmids pCZR108, pCZR112, and pCZR113 were transformed into Saccharomyces cerevisiae strain SF838-9D__tpi (ade6, his3, leu2, ura3, tpi). Glucose$^+$ Leu$^+$ transformants were analyzed for ob expression by a colony blot procedure. Transformants were picked and used to inoculate YEPD plates, overlayed with nitrocellulose filters, and grown overnight at 30° C. Filters were exposed to 0.2N NaOH, 0.1% SDS, 35 mM dithiothreitol for 30 min to lyse cells. All filters were blocked with 5% non-fat milk (NFM) in TTBS (0.1% Tween 20, 20 mM Tris pH7.5, 160 mM NaCl) for 30 min, probed with a 1/1000 dilution of affinity purified rabbit anti-murine ob (as described in Example 10) for one hour, and immune complexes were detected with a 1/1000 dilution of commercially available HRP-goat anti-rabbit (Bio-Rad, Richmond, Calif.). Filters were exposed by enhanced chemiluminescence (ECL; Amersham, Arlington Heights, Ill.), according to manufacturer's specifications. Human ob positive colonies were selected for further characterization. Yeast strains transformed with pCZR108 were designated CZY108, strains transformed with pCZR112 were designated CZY112, and strains transformed with pCZR113 were designated CZY113.

YEPD shake flask cultures were grown of CZY108, CZY112, and CZY113. 1% ethanol was added to the CZY108 culture 2 hours prior to harvest, and 1% glucose was added to the CZY112 and CZY113 cultures 4 hours prior to harvest. The yield of cells from these cultures was 20 g/L wet cell weight, which corresponds to 2 g/L total cell protein. Culture medium was analyzed directly by SDS-PAG after being mixed 1:1 in protein sample buffer (5% SDS, 8M urea, 100 mM Tris pH6.8, 2 mM EDTA, 10% glycerol) or treated with Endoglycosidase H (NEB) by adjusting the media to 0.5% SDS, 50 mM sodium citrate pH 5.2 according to the manufacturer's suggestions. 5 µl aliquots of media, corresponding to 100 µg of cells and 10 µg of total cell protein, were analyzed in all cases. Intracellular fractions were generated by glass bead disruption of 0.25 g cell pellet in 2.5 mls lysis buffer (20 mM Tris pH8.0, 400 mM NaCl, 1 mM PMSF, 2 mM EDTA, 0.1 µg/ml each of leupeptin, pepstatin, and aprotinin). Protein concentrations in lysates were determined by Lowry assay, and 10 µg were analyzed by SDS-PAGE, providing direct comparison between intracellular and extracellular levels of ob protein. For crude subcellular fractionation, Triton X100 was added to intracellular lysates to a final concentration of 2%, lysate was spun at 20,000×g for 20 min, and equal volumes of clarified lysate and pellet fraction resuspended in protein sample buffer were analyzed. Commercially available 10–20% SDS-PAGE gels (Daiichi, Tokyo, Japan) were used to separate and analyze protein samples. The gels were stained directly with Coomasie brilliant blue or Western blotted. Human ob protein on Western blots was detected with affinity purified rabbit anti-murine ob Ab in NFM-TTBS as described for colony immunoblotting above.

Transformant CZY108 produced high expression levels of human ob protein; whereas the untransformed control strain did not exhibit cross-reacting protein material. Comparison between Coomasie stained total protein of control cultures and CZY108 strains showed that the CZY108 strains produce an abundant ⁻15 kD protein. Western analysis demonstrates that this protein was human ob protein. The levels of expression were estimated to be >200 ng/10 µg total protein, or human ob expression is >2% of total cell protein. On non-readucing gels, the ob protein appears as a doublet with equal amounts of protein in each band of the doublet. This doublet collapses to a single band upon reduction, suggesting that the protein derived from cell lysates contains disulfide bonded and reduced material. Roughly 50% of the recombinant human ob protein pellets upon centrifugation at 20,00033 g. The transformants produced roughly 40 mg/L of human ob in shake flask culture.

Transformant CZY112 strains were found to mainly produce uncleaved, glycosylated α-Factor prepro:ob fusion protein, most of which was secreted from the cell and present in the cell media. Small amounts of cleaved ob with a molecular weight expected for the authentic product were produced, and most of which was retained in an intracellular compartment. Based on dilution analysis and Western blotting, there is about 2 mg/L of cleaved ob is intracellular and about 1 mg/L of cleaved ob, is found in the medium of CZY112 cells grown in shake flask.

Transformant CZY113 strains were found to produce high levels of cleaved ob protein and low levels of a protein of the size expected for an α-Factor prepro:ob fusion protein. In addition, the overall level of ob expression was elevated significantly. Coomasie staining and Western blotting revealed these cells produced a cleaved, intracellular form of human ob that was about 1% of total cell protein. The secreted levels of cleaved ob were about 5-fold lower. Gel analysis demonstrated that this form of ob migrated slightly slower than either the cytoplasmic form or the CZY112 produced form of ob. Most of the intracellular form was in the soluble phase of a sample spun at 20,000×g, suggesting it was not aggregated. The level of expression of cleaved human ob protein from CZY113 strains grown in shake flask were estimated to be 20 mg/L for the intracellular form and 4 mg/L for the secreted form.

Example 15. Distinctions Between ob Protein and ACM

A. Heat Inactivation

A preparation of Zucker rat adipose conditioned medium (ACM) was prepared as in Example 2.A., above. When tested in the ob/ob mouse bioassay, mice (n=3) injected with this ACM preparation demonstrated appetite suppression that was 49±8.6% of baseline 24 h chow intake. When this same ACM preparation was heated to 95° C. for 5 min, mice injected with this heated ACM preparation demonstrated appetite suppression that was 94±4.2% of baseline 24 h chow intake. Therefore, the active appetite suppression factor(s) in ACM were inactivated after heating at 95° C. for 5 min.

In contrast, conditioned medium containing recombinant ob protein was heat stable. Briefly, medium conditioned by BHK cells expressing recombinant ob protein was maintained at 4° C. or was heated at 95° C. for 10–20 min. Each preparation was tested in the mouse bioassay by daily intraperitoneal injections over a two week period (n=3 for each preparation tested). Each preparation of BHK/ob conditioned medium produced significant and sustained reductions in body weight and chow intake. The heated preparation retained approximately 70% of the appetite suppresive activity of the unheated preparation.

B. HPLC Analysis

Adipose-conditioned medium was subjected to HPLC and analyzed for ob protein. Briefly, a preparation of Zucker rat ACM was prepared as in Example 2.A., above. When tested in the ob/ob mouse bioassay, the mice injected with this ACM preparation demonstrated appetite suppression that was 61±11% of baseline chow intake. A 50 $\mu$l sample of this ACM preparation was injected onto a Vydac C4 HPLC column that was equilibrated in 27% acetonitrile/0.1% trifluoroacetic acid (TFA). The HPLC column was eluted using a 60 min gradient from 27% acetonitrile/0.1% TFA to 80% acetonitrile/0.1% TFA at a flow rate of 1 ml/min. Ten min fractions were collected and monitored at 215 nm, 0.2 OD full scale. The fractions were lyophilized and redissolved in 30 $\mu$l SDS-PAGE sample loading buffer (see Example 2.D.). A 15 $\mu$l aliquot of each of redissolved fractions 21–40 were electrophoresed using 10–20% Tris/Tricine gels. The gels were immunoblotted (see Example 11(2)) using an affinity-purified rabbit anti-mouse ob antibody preparation (see Example 10.B.).

Zucker rat adipose conditioned medium contained a fraction reactive with anti-ob antibodies as determined by Western blotting. This fraction eluted from the HPLC column between 31.6 and 32.6 min. This retention profile was very similar to that observed by equivalent HPLC analysis of recombinant mouse ob protein expressed in BHK cells (i.e., between 31.9 and 32.9 min). The retention time for purified, recombinant mouse ob protein that was expressed in BHK cells was 31.99 min. The estimated concentration of rat ob protein in this peak is $\leq 16$ $\mu$g/ml, as determined by comparison to a purified mouse ob standard of known protein concentration.

Upon further analysis of additional rat ACM HPLC fractions, one band detected by immunoblotting had a retention time between 20.6 and 21.6 min, and an apparent molecular weight between 43 kD (ovalbumin) and 68 kD (BSA).

C. Specific Activity

The specific activity of recombinant ob protein and ACM preparations was determined. Briefly, a 35× concentrate of medium conditioned by BHK cells expressing mouse ob protein was tested in the mouse bioassay and examined by immunoblotting. By mouse bioassay, this BHK/ob preparation demonstrated appetite suppression that was 71±10% of baseline 24 h chow intake. For immunoblotting, dilutions of a purified recombinant ob protein standard (expressed in *E. coli*; having a known protein concentration) were electrophoresed on the same gel with dilutions of the 35× BHK/ob concentrated medium. Bands corresponding to ob protein were detected using affinity-purified rabbit anti-mouse ob antibody. A 10 $\mu$l aliquot of a 1:80 dilution of 35× BHK/ob concentrate and a 10 ng ob protein standard yielded bands of similar intensity. The 35× concentrate was calculated to contain 80 $\mu$g/ml recombinant ob protein (80×10 ng of ob protein=800 ng÷10 $\mu$l of BHK/ob concentrate=80 $\mu$g/ml). The protein concentration of the same conditioned medium preparation before concentration was estimated to be about 1–2 $\mu$g/ml.

Zucker fat ACM was similarly assayed. By mouse bioassay, two distinct ACM preparations demonstrated appetite suppression that ranged from 17±5% to 57±13% of baseline 24 h chow intake. A 7.5 $\mu$l aliquot of a 28× concentrate of ACM obtained using adipose tissue from a young rat, and a 7.5 $\mu$l aliquot of a 50× concentrate of ACM obtained using adipose tissue from an old rat were electrophoresed with dilutions of the ob protein standard, and with an aliquot of 74× concentrated BHK/ob conditioned medium (appetite suppression activity=83±15% of BL For both concentrated ACM aliquots, less than 5 ng -ob protein was detected. In contrast, the concentrated BHK/ob aliquot contained >50 ng ob protein.

Preparations of BHK/ob conditioned medium and Zucker ACM were electrophoresed and silver stained, and relative amounts of protein in the predicted ob protein band were determined. Briefly, a 15× BHK/ob concentrate and a 20× concentrated ACM preparation were electrophoresed as described in Example 11. above. In the BHK/ob concentrate, a stained band was visible at the predicted ob protein location; no band was detected in the ACM preparation. Immunoblotting of the same preparations was performed. In the BHK/ob concentrate, ob protein was detected. In contrast, ob protein was only detected in the ACM preparation after a very extensive exposure period.

Taken together, these data demonstrate that significant appetite suppressive activity was present in ACM preparations that contained very low amounts of detectable ob protein. In a similarly concentrated BHK/ob preparation exhibiting less appetite suppression activity than the ACMs, at least 10× more ob protein was detected. These data suggest that additional factors or cofactors present in the ACMs (i) have appetite suppressive activity, or (ii) potentiate the activity of ob protein present in ACMs. Alternatively, these results suggest that ob protein produced and secreted in a natural adipose tissue environment is different from, and more active than, recombinant ob protein expressed in a heterologous host cell. These alternative explanations are not mutually exclusive.

D. Expected Endocrine Levels of ob Protein

In the mouse bioassay system, a significant, reproducible decrease in 24 h chow intake was observed with single, daily intraperitoneal injections of 50–100 $\mu$g recombinant ob protein. Since the recipient mice weigh approximately 50 g, the effective appetite suppressive dose in this system is in the range of about 1–2 mg/kg body weight.

In contrast, effective daily doses of insulin and glucagon in humans are in the range of about 0.01–0.02 mg/kg body weight. The relatively low potency of recombinant ob protein (2 logs less than the hormones insulin and glucagon) suggests that an additional factor or cofactor, or an in vivo modification, may be necessary to obtain a purified recombinant ob protein preparation having enhanced potentcy in vivo. These data are consistent with the results obtained in Section C., above.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. A method for inhibiting food consumption in a mammal, comprising administering an effective dose of a composition comprising an appetite suppression factor expressed by adipose tissue, wherein the factor is between about 14 kDa and 16 kDa in size as determined by SDS polyacrylamide gel electrophoresis under reducing conditions.

2. The method of claim 1, wherein the factor is essentially of a form obtainable by culturing a mammalian cell ex vivo under conditions wherein the factor is synthesized and secreted by the cell.

3. The method of claim 1, wherein the factor is obtained from adipose tissue.

4. The method of claim 1, wherein the factor is obtained from a cell containing an expression vector encoding the factor.

5. The method of claim 4, wherein the cell is a BHK cell or a CHO cell.

6. The method of claim 4, wherein the cell is a yeast cell.

7. The method of claim 1, wherein the factor is isolated.

8. A method for inhibiting food consumption in a mammal, comprising administering an effective dose of a composition comprising an appetite suppression factor expressed by adipose tissue, wherein the factor is ob protein.

9. The method of claim 8, wherein the factor is essentially of a form obtainable by culturing a mammalian cell ex vivo under conditions wherein the factor is synthesized and secreted by the cell.

10. The method of claim 8, wherein the factor is obtained from adipose tissue.

11. The method of claim 8, wherein the factor is obtained from a cell containing an expression vector encoding the factor.

12. The method of claim 11, wherein the cell is a BHK cell or a CHO cell.

13. The method of claim 11, wherein the cell is a yeast cell.

14. The method of claim 11, wherein the factor is isolated.

* * * * *

UNITED STATES PATENT AND TRADEMARK OFFICE

CERTIFICATE OF CORRECTION

PATENT NO. : 5,858,967

DATED : January 12, 1999

INVENTORS : David S. Weigle, Joseph L. Kuijer, John W. Forstrom.

It is certified that error appears in the above-identified patent and that said Letters Patent is hereby corrected as shown below:

In the title, please delete "SUPRESSION" and insert --SUPPRESSION--;

On front page, at [63], line 2-3, please delete "July 10, 1995" and insert --April 10, 1995--;

On front page, second column, under OTHER PUBLICATIONS at Ngo et al., please delete "Pediction" and inert --Prediction--;

Column 1, line 45, please delete "Liebel" and insert --Liebelt--;

Column 4, line 36, please delete "3083" and insert --1083--;

Column 8, line 12, please delete "preciously" and insert --previously--;

Column 22, line 21, plese delete "specfication" and insert --specification--;

Column 26, line 54, please delete "mercapt-ethanol" and insert --mercaptoethanol--;

Column 27, line 16, please delete "CDNA" and insert --cDNA--;

line 19, please delete "CDNA" and insert --cDNA--;

UNITED STATES PATENT AND TRADEMARK OFFICE
CERTIFICATE OF CORRECTION

PATENT NO. : 5,858,967
DATED : January 12, 1999
INVENTOR(S) : David S. Weigle, Joseph L. Kuijer, John W. Forstrom.

It is certified that error appears in the above-identified patent and that said Letters Patent is hereby corrected as shown below:

Column 32, line 11, please delete "enyzmes" and insert --enzymes--;

Column 32, line 16, please delete second appearance of "to";

line 60, please delete "react-on" and insert --reaction--;

Column 34, line 20, please delete "20,00033 g" and insert --20,000xg--;

In the claims, Claim 14, please delete "11" and insert --8--.

Signed and Sealed this

Fifth Day of September, 2000

*Attest:*

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 504 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..501

( x i ) SEQUENCE DESCRIPTION: SEQ ID NO:1:

```
ATG TGC TGG AGA CCC CTG TGT CGG TTC CTG TGG CTT TGG TCC TAT CTG       48
Met Cys Trp Arg Pro Leu Cys Arg Phe Leu Trp Leu Trp Ser Tyr Leu
 1               5                  10                  15

TCT TAT GTT CAA GCA GTG CCT ATC CAG AAA GTC CAG GAT GAC ACC AAA       96
Ser Tyr Val Gln Ala Val Pro Ile Gln Lys Val Gln Asp Asp Thr Lys
             20                  25                  30

ACC CTC ATC AAG ACC ATT GTC ACC AGG ATC AAT GAC ATT TCA CAC ACG      144
Thr Leu Ile Lys Thr Ile Val Thr Arg Ile Asn Asp Ile Ser His Thr
         35                  40                  45

CAG TCG GTA TCC GCC AAG CAG AGG GTC ACT GGC TTG GAC TTC ATT CCT      192
Gln Ser Val Ser Ala Lys Gln Arg Val Thr Gly Leu Asp Phe Ile Pro
     50                  55                  60

GGG CTT CAC CCC ATT CTG AGT TTG TCC AAG ATG GAC CAG ACT CTG GCA      240
Gly Leu His Pro Ile Leu Ser Leu Ser Lys Met Asp Gln Thr Leu Ala
 65                  70                  75                  80

GTC TAT CAA CAG GTC CTC ACC AGC CTG CCT TCC CAA AAT GTG CTG CAG      288
Val Tyr Gln Gln Val Leu Thr Ser Leu Pro Ser Gln Asn Val Leu Gln
                 85                  90                  95

ATA GCC AAT GAC CTG GAG AAT CTC CGA GAC CTC CTC CAT CTG CTG GCC      336
Ile Ala Asn Asp Leu Glu Asn Leu Arg Asp Leu Leu His Leu Leu Ala
            100                 105                 110

TTC TCC AAG AGC TGC TCC CTG CCT CAG ACC AGT GGC CTG CAG AAG CCA      384
Phe Ser Lys Ser Cys Ser Leu Pro Gln Thr Ser Gly Leu Gln Lys Pro
        115                 120                 125

GAG AGC CTG GAT GGC GTC CTG GAA GCC TCA CTC TAC TCC ACA GAG GTG      432
Glu Ser Leu Asp Gly Val Leu Glu Ala Ser Leu Tyr Ser Thr Glu Val
    130                 135                 140

GTG GCT TTG AGC AGG CTG CAG GGC TCT CTG CAG GAC ATT CTT CAA CAG      480
Val Ala Leu Ser Arg Leu Gln Gly Ser Leu Gln Asp Ile Leu Gln Gln
145                 150                 155                 160

TTG GAT GTT AGC CCT GAA TGC TGA                                      504
Leu Asp Val Ser Pro Glu Cys
                165
```

( 2 ) INFORMATION FOR SEQ ID NO:2:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met<br>1 | Cys | Trp | Arg | Pro<br>5 | Leu | Cys | Arg | Phe | Leu<br>10 | Trp | Leu | Trp | Ser | Tyr<br>15 | Leu |
|---|---|---|---|---|---|---|---|---|---|---|---|---|---|---|---|
| Ser | Tyr | Val | Gln<br>20 | Ala | Val | Pro | Ile | Gln<br>25 | Lys | Val | Gln | Asp | Asp<br>30 | Thr | Lys |
| Thr | Leu | Ile<br>35 | Lys | Thr | Ile | Val | Thr<br>40 | Arg | Ile | Asn | Asp | Ile<br>45 | Ser | His | Thr |
| Gln | Ser<br>50 | Val | Ser | Ala | Lys | Gln<br>55 | Arg | Val | Thr | Gly | Leu<br>60 | Asp | Phe | Ile | Pro |
| Gly<br>65 | Leu | His | Pro | Ile | Leu<br>70 | Ser | Leu | Ser | Lys | Met<br>75 | Asp | Gln | Thr | Leu | Ala<br>80 |
| Val | Tyr | Gln | Gln | Val<br>85 | Leu | Thr | Ser | Leu | Pro<br>90 | Ser | Gln | Asn | Val | Leu<br>95 | Gln |
| Ile | Ala | Asn | Asp<br>100 | Leu | Glu | Asn | Leu | Arg<br>105 | Asp | Leu | Leu | His | Leu<br>110 | Leu | Ala |
| Phe | Ser | Lys<br>115 | Ser | Cys | Ser | Leu | Pro<br>120 | Gln | Thr | Ser | Gly | Leu<br>125 | Gln | Lys | Pro |
| Glu | Ser<br>130 | Leu | Asp | Gly | Val | Leu<br>135 | Glu | Ala | Ser | Leu | Tyr<br>140 | Ser | Thr | Glu | Val |
| Val<br>145 | Ala | Leu | Ser | Arg | Leu<br>150 | Gln | Gly | Ser | Leu | Gln<br>155 | Asp | Ile | Leu | Gln | Gln<br>160 |
| Leu | Asp | Val | Ser | Pro<br>165 | Glu | Cys | | | | | | | | | |

( 2 ) INFORMATION FOR SEQ ID NO:3:

( i ) SEQUENCE CHARACTERISTICS:
        ( A ) LENGTH: 966 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 46..546

( x i ) SEQUENCE DESCRIPTION: SEQ ID NO:3:

| GCGCCAGCGG | TTGCAAGGCC | CAAGAAGCCC | ATCCTGGGAA | GGAAA | ATG | CAT | TGG | 54 |
|---|---|---|---|---|---|---|---|---|
| | | | | | Met<br>1 | His | Trp | |

| GGA | ACC | CTG | TGC | GGA | TTC | TTG | TGG | CTT | TGG | CCC | TAT | CTT | TTC | TAT | GTC | 102 |
|---|---|---|---|---|---|---|---|---|---|---|---|---|---|---|---|---|
| Gly | Thr<br>5 | Leu | Cys | Gly | Phe | Leu<br>10 | Trp | Leu | Trp | Pro | Tyr<br>15 | Leu | Phe | Tyr | Val | |

| CAA | GCT | GTG | CCC | ATC | CAA | AAA | GTC | CAA | GAT | GAC | ACC | AAA | ACC | CTC | ATC | 150 |
|---|---|---|---|---|---|---|---|---|---|---|---|---|---|---|---|---|
| Gln | Ala | Val | Pro | Ile | Gln | Lys | Val | Gln | Asp | Asp | Thr | Lys | Thr | Leu | Ile | |
| 20 | | | | | 25 | | | | | 30 | | | | | 35 | |

| AAG | ACA | ATT | GTC | ACC | AGG | ATC | AAT | GAC | ATT | TCA | CAC | ACG | CAG | TCA | GTC | 198 |
|---|---|---|---|---|---|---|---|---|---|---|---|---|---|---|---|---|
| Lys | Thr | Ile | Val | Thr<br>40 | Arg | Ile | Asn | Asp | Ile<br>45 | Ser | His | Thr | Gln | Ser<br>50 | Val | |

| TCC | TCC | AAA | CAG | AAA | GTC | ACC | GGT | TTG | GAC | TTC | ATT | CCT | GGG | CTC | CAC | 246 |
|---|---|---|---|---|---|---|---|---|---|---|---|---|---|---|---|---|
| Ser | Ser | Lys | Gln<br>55 | Lys | Val | Thr | Gly | Leu<br>60 | Asp | Phe | Ile | Pro | Gly<br>65 | Leu | His | |

| CCC | ATC | CTG | ACC | TTA | TCC | AAG | ATG | GAC | CAG | ACA | CTG | GCA | GTC | TAC | CAA | 294 |
|---|---|---|---|---|---|---|---|---|---|---|---|---|---|---|---|---|
| Pro | Ile | Leu<br>70 | Thr | Leu | Ser | Lys | Met<br>75 | Asp | Gln | Thr | Leu | Ala<br>80 | Val | Tyr | Gln | |

| CAG | ATC | CTC | ACC | AGT | ATG | CCT | TCC | AGA | AAC | GTG | ATC | CAA | ATA | TCC | AAC | 342 |
|---|---|---|---|---|---|---|---|---|---|---|---|---|---|---|---|---|
| Gln | Ile<br>85 | Leu | Thr | Ser | Met | Pro<br>90 | Ser | Arg | Asn | Val | Ile<br>95 | Gln | Ile | Ser | Asn | |

| GAC | CTG | GAG | AAC | CTC | CGG | GAT | CTT | CTT | CAC | GTG | CTG | GCC | TTC | TCT | AAG | 390 |
|---|---|---|---|---|---|---|---|---|---|---|---|---|---|---|---|---|
| Asp | Leu | Glu | Asn | Leu | Arg | Asp | Leu | Leu | His | Val | Leu | Ala | Phe | Ser | Lys | |

```
                   100                      105                      110                     115
AGC  TGC  CAC  TTG  CCC  TGG  GCC  AGT  GGC  CTG  GAG  ACC  TTG  GAC  AGC  CTG                438
Ser  Cys  His  Leu  Pro  Trp  Ala  Ser  Gly  Leu  Glu  Thr  Leu  Asp  Ser  Leu
               120                      125                          130

GGG  GGT  GTC  CTG  GAA  GCT  TCA  GGC  TAC  TCC  ACA  GAG  GTG  GTG  GCC  CTG                486
Gly  Gly  Val  Leu  Glu  Ala  Ser  Gly  Tyr  Ser  Thr  Glu  Val  Val  Ala  Leu
               135                      140                          145

AGC  AGG  CTG  CAG  GGG  TCT  CTG  CAG  GAC  ATG  CTG  TGG  CAG  CTG  GAC  CTC                534
Ser  Arg  Leu  Gln  Gly  Ser  Leu  Gln  Asp  Met  Leu  Trp  Gln  Leu  Asp  Leu
               150                      155                          160

AGC  CCT  GGG  TGC  TGAGGCCTTG  AAGGTCACTC  TTCCTGCAAG  GACTACGTTA                            586
Ser  Pro  Gly  Cys
               165

AGGGAAGGAA  CTCTGGCTTC  CAGGTATCTC  CAGGATTGAA  GAGCATTGCA  TGGACACCCC                        646

TTATCCAGGA  CTCTGTCAAT  TTCCCTGACT  CCTCTAAGCC  ACTCTTCCAA  AGGCATAAGA                        706

CCCTAAGCCT  CCTTTTGCTT  GAAACCAAAG  ATATATACAC  AGGATCCTAT  TCTCACCAGG                        766

AAGGGGGTCC  ACCCAGCAAA  GAGTGGGCTG  CATCTGGGAT  TCCCACCAAG  GTCTTCAGCC                        826

ATCAACAAGA  GTTGTCTTGT  CCCCTCTTGA  CCCATCTCCC  CCTCACTGAA  TGCCTCAATG                        886

TGACCAGGGG  TGATTTCAGA  GAGGGCAGAG  GGGTAGGCAG  AGCCTTTGGA  TGACCAGAAC                        946

AAGGTTCCCT  CTGAGAATTC                                                                        966
```

( 2 ) INFORMATION FOR SEQ ID NO:4:

( i ) SEQUENCE CHARACTERISTICS:
        ( A ) LENGTH: 167 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  His  Trp  Gly  Thr  Leu  Cys  Gly  Phe  Leu  Trp  Leu  Trp  Pro  Tyr  Leu
 1                  5                   10                      15

Phe  Tyr  Val  Gln  Ala  Val  Pro  Ile  Gln  Lys  Val  Gln  Asp  Asp  Thr  Lys
               20                       25                      30

Thr  Leu  Ile  Lys  Thr  Ile  Val  Thr  Arg  Ile  Asn  Asp  Ile  Ser  His  Thr
               35                       40                      45

Gln  Ser  Val  Ser  Ser  Lys  Gln  Lys  Val  Thr  Gly  Leu  Asp  Phe  Ile  Pro
      50                       55                      60

Gly  Leu  His  Pro  Ile  Leu  Thr  Leu  Ser  Lys  Met  Asp  Gln  Thr  Leu  Ala
65                           70                      75                      80

Val  Tyr  Gln  Gln  Ile  Leu  Thr  Ser  Met  Pro  Ser  Arg  Asn  Val  Ile  Gln
                    85                       90                      95

Ile  Ser  Asn  Asp  Leu  Glu  Asn  Leu  Arg  Asp  Leu  Leu  His  Val  Leu  Ala
                    100                      105                     110

Phe  Ser  Lys  Ser  Cys  His  Leu  Pro  Trp  Ala  Ser  Gly  Leu  Glu  Thr  Leu
               115                      120                     125

Asp  Ser  Leu  Gly  Gly  Val  Leu  Glu  Ala  Ser  Gly  Tyr  Ser  Thr  Glu  Val
      130                      135                      140

Val  Ala  Leu  Ser  Arg  Leu  Gln  Gly  Ser  Leu  Gln  Asp  Met  Leu  Trp  Gln
145                      150                      155                     160

Leu  Asp  Leu  Ser  Pro  Gly  Cys
                    165
```

( 2 ) INFORMATION FOR SEQ ID NO:5:

(i) SEQUENCE CHARACTERISTICS:
    (A) LENGTH: 438 base pairs
    (B) TYPE: nucleic acid
    (C) STRANDEDNESS: double
    (D) TOPOLOGY: linear (ii) MOLECULE TYPE: cDNA (ix) FEATURE:
    (A) NAME/KEY: CDS
    (B) LOCATION: 1..435

(xi) SEQUENCE DESCRIPTION: SEQ ID NO:5:

| GTC | CCT | ATC | CAG | AAA | GTC | CAG | GAT | GAC | ACC | AAA | ACC | CTC | ATC | AAG | ACC | 48 |
| Val | Pro | Ile | Gln | Lys | Val | Gln | Asp | Asp | Thr | Lys | Thr | Leu | Ile | Lys | Thr | |
| 1 | | | | 5 | | | | | 10 | | | | | 15 | | |

| ATT | GTC | ACC | AGG | ATC | AAT | GAC | ATT | TCA | CAC | ACG | TCG | GTA | TCC | GCC | AAG | 96 |
| Ile | Val | Thr | Arg | Ile | Asn | Asp | Ile | Ser | His | Thr | Ser | Val | Ser | Ala | Lys | |
| | | | 20 | | | | | 25 | | | | | 30 | | | |

| CAG | AGG | GTC | ACT | GGC | TTG | GAC | TTC | ATT | CCT | GGG | CTT | CAC | CCC | ATT | CTG | 144 |
| Gln | Arg | Val | Thr | Gly | Leu | Asp | Phe | Ile | Pro | Gly | Leu | His | Pro | Ile | Leu | |
| | | | 35 | | | | | 40 | | | | | 45 | | | |

| AGT | TTG | TCC | AAG | ATG | GAC | CAG | ACT | CTG | GCA | GTC | TAT | CAA | CAG | GTC | CTC | 192 |
| Ser | Leu | Ser | Lys | Met | Asp | Gln | Thr | Leu | Ala | Val | Tyr | Gln | Gln | Val | Leu | |
| | 50 | | | | | 55 | | | | | 60 | | | | | |

| ACC | AGC | CTG | CCT | TCC | CAA | AAT | GTG | CTG | CAG | ATA | GCC | AAT | GAC | CTG | GAG | 240 |
| Thr | Ser | Leu | Pro | Ser | Gln | Asn | Val | Leu | Gln | Ile | Ala | Asn | Asp | Leu | Glu | |
| 65 | | | | | 70 | | | | | 75 | | | | | 80 | |

| AAT | CTC | CGA | GAC | CTC | CTC | CAT | CTG | CTG | GCC | TTC | TCC | AAG | AGC | TGC | TCC | 288 |
| Asn | Leu | Arg | Asp | Leu | Leu | His | Leu | Leu | Ala | Phe | Ser | Lys | Ser | Cys | Ser | |
| | | | | 85 | | | | | 90 | | | | | 95 | | |

| CTG | CCT | CAG | ACC | AGT | GGC | CTG | CAG | AAG | CCA | GAG | AGC | CTG | GAT | GGC | GTC | 336 |
| Leu | Pro | Gln | Thr | Ser | Gly | Leu | Gln | Lys | Pro | Glu | Ser | Leu | Asp | Gly | Val | |
| | | | 100 | | | | | 105 | | | | | 110 | | | |

| CTG | GAA | GCC | TCA | CTC | TAC | TCC | ACA | GAG | GTG | GTG | GCT | TTG | AGC | AGG | CTG | 384 |
| Leu | Glu | Ala | Ser | Leu | Tyr | Ser | Thr | Glu | Val | Val | Ala | Leu | Ser | Arg | Leu | |
| | | | 115 | | | | | 120 | | | | | 125 | | | |

| CAG | GGC | TCT | CTG | CAG | GAC | ATT | CTT | CAA | CAG | TTG | GAT | GTT | AGC | CCT | GAA | 432 |
| Gln | Gly | Ser | Leu | Gln | Asp | Ile | Leu | Gln | Gln | Leu | Asp | Val | Ser | Pro | Glu | |
| | 130 | | | | | 135 | | | | | 140 | | | | | |

| TGC | TGA | | | | | | | | | | | | | | | 438 |
| Cys | | | | | | | | | | | | | | | | |
| 145 | | | | | | | | | | | | | | | | |

(2) INFORMATION FOR SEQ ID NO:6:

(i) SEQUENCE CHARACTERISTICS:
    (A) LENGTH: 145 amino acids
    (B) TYPE: amino acid
    (D) TOPOLOGY: linear (ii) MOLECULE TYPE: protein (xi) SEQUENCE DESCRIPTION: SEQ ID NO:6:

| Val | Pro | Ile | Gln | Lys | Val | Gln | Asp | Asp | Thr | Lys | Thr | Leu | Ile | Lys | Thr |
| 1 | | | | 5 | | | | | 10 | | | | | 15 | |

| Ile | Val | Thr | Arg | Ile | Asn | Asp | Ile | Ser | His | Thr | Ser | Val | Ser | Ala | Lys |
| | | | 20 | | | | | 25 | | | | | 30 | | |

| Gln | Arg | Val | Thr | Gly | Leu | Asp | Phe | Ile | Pro | Gly | Leu | His | Pro | Ile | Leu |
| | | | 35 | | | | | 40 | | | | | 45 | | |

| Ser | Leu | Ser | Lys | Met | Asp | Gln | Thr | Leu | Ala | Val | Tyr | Gln | Gln | Val | Leu |
| | 50 | | | | | 55 | | | | | 60 | | | | |

| Thr | Ser | Leu | Pro | Ser | Gln | Asn | Val | Leu | Gln | Ile | Ala | Asn | Asp | Leu | Glu |
| 65 | | | | | 70 | | | | | 75 | | | | | 80 |

```
Asn  Leu  Arg  Asp  Leu  Leu  His  Leu  Leu  Ala  Phe  Ser  Lys  Ser  Cys  Ser
               85                  90                            95

Leu  Pro  Gln  Thr  Ser  Gly  Leu  Gln  Lys  Pro  Glu  Ser  Leu  Asp  Gly  Val
              100                 105                      110

Leu  Glu  Ala  Ser  Leu  Tyr  Ser  Thr  Glu  Val  Val  Ala  Leu  Ser  Arg  Leu
         115                      120                      125

Gln  Gly  Ser  Leu  Gln  Asp  Ile  Leu  Gln  Gln  Leu  Asp  Val  Ser  Pro  Glu
    130                      135                 140

Cys
145
```

(2) INFORMATION FOR SEQ ID NO:7:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:7:

TAAAAGAAT  TCAAAAATGG  TGCCCATCCA  AAAAGTCCAA    40

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:8:

ACGACTGTCG  ACTCAGCACC  CAGGGCTGAG    30

(2) INFORMATION FOR SEQ ID NO:9:

(i) SEQUENCE CHARACTERISTICS:
        (A) LENGTH: 43 base pairs
        (B) TYPE: nucleic acid
        (C) STRANDEDNESS: single
        (D) TOPOLOGY: linear (xi) SEQUENCE DESCRIPTION: SEQ ID NO:9:

GAACAGAAGC  TTGGACAAGA  GAGTGCCCAT  CCAAAAAGTC  CAA    43

(2) INFORMATION FOR SEQ ID NO:10:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:10:

GAACAGAAGC  TTGGACAAGA  GAGAAGCTGT  GCCCATCCAA  AAAGTCCAA    49